United States Patent
Morra

(10) Patent No.: US 12,109,246 B2
(45) Date of Patent: Oct. 8, 2024

(54) COMPOSITION FOR THE TREATMENT AND/OR PREVENTION OF LOWER URINARY TRACT SYMPTOMS

(71) Applicant: SERELYS PHARMA S.A.M., Monaco (MC)

(72) Inventor: Sossio Morra, Monaco (MC)

(73) Assignee: SÉRÉLYS PHARMA S.A.M., Monaco (MC)

( * ) Notice: Subject to any disclaimer, the term of this patent is extended or adjusted under 35 U.S.C. 154(b) by 594 days.

(21) Appl. No.: 17/365,055

(22) PCT Filed: Jan. 13, 2020

(86) PCT No.: PCT/EP2020/050671
§ 371 (c)(1),
(2) Date: Jul. 1, 2021

(87) PCT Pub. No.: WO2020/148224
PCT Pub. Date: Jul. 23, 2020

(65) Prior Publication Data
US 2023/0149498 A1 May 18, 2023

(30) Foreign Application Priority Data
Jan. 18, 2019 (FR) ...................................... 1900478

(51) Int. Cl.
*A61K 36/899* (2006.01)
*A61K 9/00* (2006.01)
*A61K 31/355* (2006.01)
*A61K 36/15* (2006.01)
*A61K 36/42* (2006.01)
*A61K 45/06* (2006.01)
*A61P 13/10* (2006.01)

(52) U.S. Cl.
CPC .......... *A61K 36/899* (2013.01); *A61K 9/0053* (2013.01); *A61K 31/355* (2013.01); *A61K 36/15* (2013.01); *A61K 36/42* (2013.01); *A61K 45/06* (2013.01); *A61P 13/10* (2018.01); *A61K 2236/331* (2013.01)

(58) Field of Classification Search
CPC ...... A61K 36/15; A61K 31/355; A61K 36/42; A61K 9/0053; A61K 39/36; A61K 36/899; A61P 37/08
See application file for complete search history.

(56) References Cited

U.S. PATENT DOCUMENTS 11,253,563 B2 * 2/2022 Morra .................. A61K 31/593

FOREIGN PATENT DOCUMENTS

| FR | 3055215 A1 | 3/2018 | |
|---|---|---|---|
| FR | 3068605 A1 | 1/2019 | |
| FR | 3068605 B1 * | 2/2020 | ........... A61K 31/355 |

OTHER PUBLICATIONS

History of Changes for Study: NCT03438422, Oct. 22, 2018, https://clinicaltrials.gov/ct2/history/NCT03438422?V_2=View#StudyPageTop, retrieved Sep. 10, 2019.
William Faloon, A Breakthrough in the Relief of Overactive Bladder and Urinary Incontinence—Underlying Cause of Urinary Miseries, Nov. 1, 2008, https://pdfs.semanticscholar.org/f44f/9a1cb2cd8a6d1d559d7c29ed79cc22579398.pdf, retrieved on Sep. 10, 2019.
WO, English Translation of International Search Report; PCT/EP2020/050671, Jul. 23, 2020 (3 pages).

* cited by examiner

*Primary Examiner* — Kyle A Purdy
(74) *Attorney, Agent, or Firm* — FisherBroyles, LLP; Susan M. Oiler

(57) ABSTRACT

Compositions for treatment and/or prevention of lower urinary tract symptoms (LUTS). include a pollen extract containing an aqueous pollen extract obtained from a plant mixture belonging to the Poaceae and Pionaceae families, an aqueous extract of plant seeds belonging to the genus *Cucurbita* and of vitamin E or its esters. Methods for treatment and/or prevention of lower urinary tract symptoms (LUTS) associated with the filling, urination and/or post-urination phases in women with such compositions is disclosed.

15 Claims, 10 Drawing Sheets

COMPOSITION FOR THE TREATMENT AND/OR PREVENTION OF LOWER URINARY TRACT SYMPTOMS

CROSS-REFERENCE TO RELATED APPLICATIONS

The present invention is filed under 35 U.S.C. § 371 as the U.S. national phase of International Patent Application No. PCT/EP2020/050671, filed Jan. 13, 2020, which designated the United States and which claims the benefit of French Patent Application No. 1900478, filed Jan. 18, 2019, which is hereby incorporated in its entirety including all tables, figures, and claims.

TECHNICAL FIELD

The present invention relates to a composition based on plant extracts for use in the treatment and/or prevention of Lower Urinary Tract Symptoms (LUTS).

Lower Urinary Tract Symptoms (LUTS) are common in men and women of all ages. The prevalence and severity of LUTS increase with age and are a major problem in the aging population. It is now accepted that LUTS are a group of progressive, age-related, non-gender or organ-specific symptoms that include a combination of symptoms of filling, micturition and post-micturition phases.

One of the main symptoms is urinary incontinence. It is known (DeMaagd et al., "Management of Urinary Incontinence", P&T®, June 2012, Vol. 37 No. 6) that approximately 10 million patients in the United States have urinary incontinence. For example, in 2007, it is estimated that more than 25 million people in the United States experienced episodes of urinary incontinence. It appears that the prevalence of urinary incontinence is higher in women than in men aged 80 or younger, but men and women are affected almost equally after the age of 80.

LUTS can have multiple causes located in the urinary tract or at a distance therefrom. LUTS can result from infections and inflammation (e.g. cystitis, prostatitis), from a structural condition (e.g. stones, tumours, prolapse, benign prostatic hypertrophy), from a medical problem (e.g. diabetes mellitus, multiple sclerosis) or drug use (e.g. anticholinergics, opioids).

Although LUTS do not generally cause serious illness, they are a frequent reason for medical attention, can severely affect quality of life, and be an indication of serious urinary tract disease. These LUTS can be responsible for complications and can be, for example, associated with sexual dysfunction, depression, hypertension and anxiety.

Due to the etiological complexity, the treatments for LUTS must therefore be adapted to each patient, and take into account the type and intensity of symptoms, their progression, the existence of comorbidities and the quality of life of the patients. In addition, the personal opinion of patients should be taken into account.

Not all people with LUTS need treatment.

However, it may be necessary to resort to pharmaceutical treatments or even surgery to treat LUTS.

BACKGROUND

The pharmaceutical treatment of choice for a patient with moderate to severe symptoms, which have an effect on the quality of life, is an alpha-blocker monotherapy. They are alpha-adrenergic receptor agonists. They work by relaxing the smooth muscle fibres of the bladder neck and prostate in men and/or the proximal urethra in women. Their action is rapid and stable over several years, with a significant improvement in LUTS.

However, alpha-blockers have significant side effects such as orthostatic hypotension, headaches, dizziness or accommodation disorders. They must also be prescribed with caution in elderly patients, coronary patients, and in the event of associated antihypertensive treatment. They are contra-indicated before cataract surgery or in the event of a history of orthostatic hypotension.

5-alpha-reductase inhibitors (I5AR) are second line pharmaceuticals. They are used more particularly in men and block the conversion of testosterone to dihydrotestosterone (DHT), which is the active metabolite for prostate growth. Their efficacy has been demonstrated on symptoms, flow, reduced risk of acute urine retention, reduced need for surgery, and a 20% reduction in prostate volume.

However, their action is slow, between 3 and 6 months, and they cause sexual disorders (reduced libido, erectile dysfunction, gynaecomastia).

The combination therapy between an alpha-blocker and a 5-alpha-reductase inhibitor is more effective in the long term on urinary symptoms than either of the monotherapies, but the side effects are cumulative.

Other treatments are known using anticholinergics (antimuscarinics) or phosphodiesterase type 5 inhibitors (IPDE5).

However, they are only of limited efficacy, for example in urgent cases for anticholinergics, while causing undesirable effects such as dry mouth, constipation, confusion, and especially increased dysuria.

Collagen is also known to be used especially in the treatment of urinary incontinence in women.

However, collagen is administered by injection, which requires intervention and may reduce compliance.

Herbal medicine is also used in the treatment of LUTS. These are treatments based on plant extracts that have excellent tolerance due to the absence of side effects. The most widely used molecules are extracted from *Pygeum africanum* and *Serenoa repens*.

Nevertheless, even if the literature is contradictory on their subject, their efficacy with regard to LUTS, although significant, remains modest. Their combination with other treatments is not recommended.

For this purpose, compositions are known for maintaining the health of the prostate in men.

Known, for example, are the publications by H. G. Preuss et al. ("A Critical Review of Cernitin™ for Symptomatic Relief Of Lower Urinary Tract Symptoms (LUTS) in Men", RESEARCH COMMUNICATIONS IN PHARMACOLOGY AND TOXICOLOGY, 2013) or W. G. Chambliss et al. ("Flower Pollen Extract and its Effects on Urinary Support, Bladder and Smooth Muscle Contents", 2013), which disclose the activity of CERNITIN™ (=GRAMINEX® Flower Pollen Extract) in men with benign prostatic hypertrophy which may cause lower urinary tract symptoms or present other disorders related to the prostate. CERNITIN™ is a mixture of pollen of rye (*Secale cereale* L.), timothy grass (*Phleum pratense*) and maize (*Zea mays* L.), comprising an aqueous extract and an oily extract of pollen in a 20:1 ratio.

Other compositions based on GRAMINEX® comprising, for example, in particular an extract of pumpkin seeds containing 25% fatty acids ("Prostate Support—Weil Vitamin Advisor", 2016) or an extract of pumpkin seeds standardised to 10% fatty acids and vitamin E (PROSTA-CERN™) are known to support prostate-related problems in men.

Such products are therefore primarily intended for men with prostate-related problems.

Men may experience incontinence problems in this regard, but the reasons differ from those for women. These are mainly:

- disorders related to the prostate such as an increase in its volume (prostatic hypertrophy), which compresses the urethra. The male subject then suffers from the occurrence of delayed drops or even nocturnal urine leaks;
- prostatectomy: which is the removal of the prostate;
- health problems such as a tumour of the urethra or urethral stricture which is defined by the narrowing of the urethra and which obstructs the usual urinary flow.

However, even though disorders related to the prostate in general can result in lower urinary tract symptoms, such compositions do not appear, prima facie, to be directly indicated for the treatment and/or prevention of LUTS, and more particularly urinary incontinence, in women.

However, the product PURE™ Control C/P ("Incontinence, frequent urination, bladder health—Women Living Naturally", 17 Jun. 2017) is known for the treatment of urinary incontinence in women. It consists of an extract of CERNITIN™ pollen (mixture of pollen of rye (*Secale cereale* L.), timothy grass (*Phleum pratense*) and maize (*Zea mays* L.) comprising an aqueous extract and an oily extract of pollen in a ratio of 20:1) and an extract of pumpkin seeds standardised not to contain fatty acids but lignans and phenolic derivatives. It appears that such a fatty acid-free pumpkin seed extract (usually known to have a high fatty acid content) helps maintain healthy urination during the day and at night after 6 weeks of treatment in post-menopausal women.

Technical Problem

Considering the above, in order to resolve the known problems linked to the adverse effects of the treatments used, and to improve the efficacy against LUTS, in particular urinary incontinence, and this specifically in women in the broad sense, for example of women aged 16 to 75, while exhibiting excellent tolerance, the Applicant has developed a new composition based on plant extracts.

In addition, mastering the manufacturing parameters of plant extracts ensures traceability, standardisation and reproducibility framed by a specification of the extracts.

Technical Solution

The solution to the problem posed by the present invention relates to a composition comprising a pollen extract containing an aqueous pollen extract obtained from a plant mixture belonging to the Pinaceae and Poaceae family, an aqueous extract of plant seeds belonging to the genus *Cucurbita* and vitamin E or its esters, for use in the treatment and/or prevention of lower urinary tract symptoms (LUTS) in women.

Advantages Provided

The Applicant has been able to demonstrate that the use of the composition which is the subject of the invention makes it possible in particular to prevent or improve the lower urinary tract symptoms (LUTS) associated with the filling, micturition and/or post-micturition phases in women, regardless of their age, and more preferably still urinary incontinence, in particular the treatment and/or prevention of stress urinary incontinence (SUI), urinary incontinence due to urgency (or urge) and mixed urinary incontinence (MUI), including in particular the reduction in the frequency of nocturnal micturition inducing an awakening.

BRIEF DESCRIPTION OF THE DRAWINGS

The invention and the advantages resulting therefrom will be better understood by reading the following description and non-limiting embodiments, illustrated with reference to the appended drawings in which.

DETAILED DESCRIPTION

Figure 1:
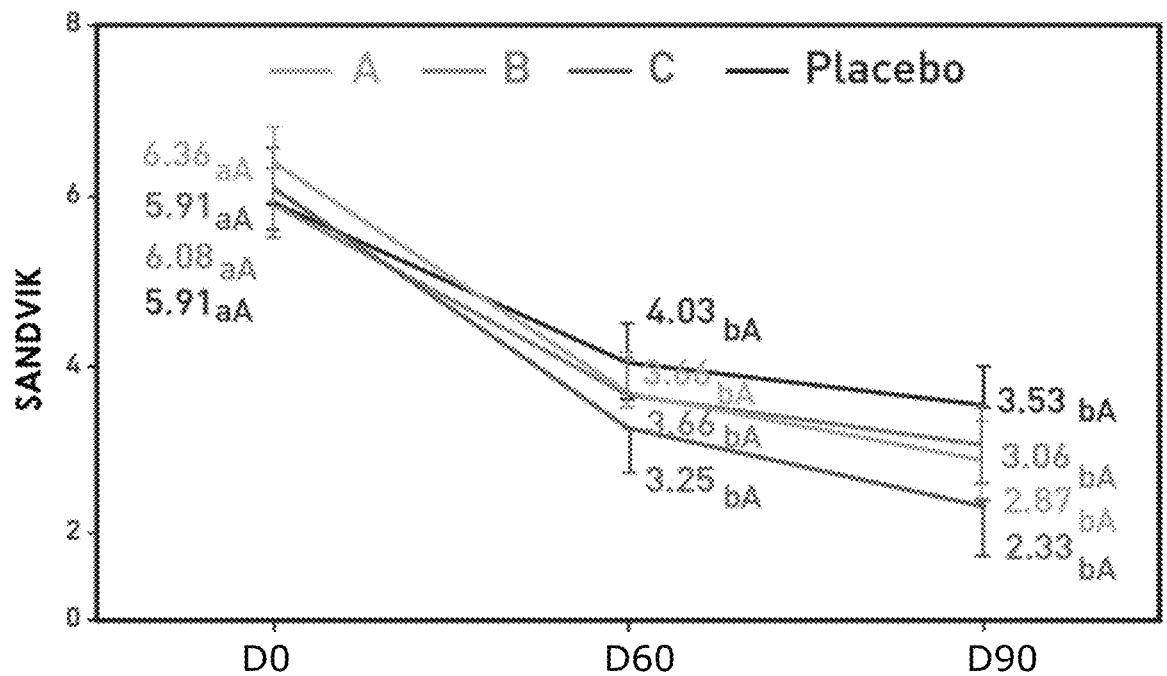
FIG. 1 shows the results obtained with the SANDVIK scale in a comparative manner with different compositions in the context of the study according to Example 5 on urinary incontinence in women before treatment (D0), after 60 days of treatment (D60) and after 90 days of treatment (D90).

In this description, unless otherwise specified, it is understood that, when an interval is given, it includes the upper and lower limits of said interval.

The invention relates to a composition used in the treatment and/or prevention of lower urinary tract symptoms (LUTS) in women comprising a pollen extract containing an aqueous pollen extract obtained from a plant mixture belonging to the Pinaceae and Poaceae family, an aqueous extract of plant seeds belonging to the genus *Cucurbita* and vitamin E or its esters.

The term "treatment" refers to an improvement, prophylaxis or reversal of a disease or disorder, or at least one discernible symptom thereof. It is also an improvement, prophylaxis or reversal of at least one measurable physical parameter related to the disease or disorder being treated, which is not necessarily perceptible by the subject. In another embodiment, the term "treatment" refers to inhibiting or slowing the progression of a disease or disorder, either physically, for example, stabilising a discernible symptom, physiologically, for example, stabilising a physical parameter, or both. The term "treatment" also refers to the delay in the onset of a disease or disorder. In some particular embodiments of the invention, the composition of interest is administered as a preventative measure. In this context, the term "prevention" refers to a reduction in the risk of acquiring a specified disease or disorder.

By pollen extract according to the invention is meant a pollen extract containing an aqueous pollen extract obtained from a mixture of plants belonging to the Pinaceae and Poaceae family.

Poaceae, also called Gramineae, is a family of monocotyledonous plants of the order Poales. The customary name is "Poaceae" or "Grasses". This family, made up of about 12,000 species grouped into 780 genera, includes most of the species commonly known as "herbs" and "cereals". They are generally herbaceous plants, more rarely woody (bamboo).

Like all anemophilous pollen, Poaceae pollen is spherical or slightly ellipsoidal in shape with reduced ornamentation. The single aperture (or pore) is round: this is one of the criteria for monocotyledons. Poaceae pollen is small in size and light. The size is around 40 microns. For cereals, the size is 60 to 100 microns.

The family of Pinaceae (Pinaceae), or Abietaceae, includes gymnosperm plants; it has 220-250 species divided into 11 genera. They are trees or shrubs, from temperate regions, either with evergreen leaves in needle or scale form, or deciduous like those of larches. In this family, the species native to France are found among the genera *Abies* (fir trees), *Picea* (spruces), *Larix* (European larch), and *Pinus* (pines).

Pinaceae produce large grains of pollen abundantly, usually between 40 and 100 microns in size. They are devoid of pores. The pollen grains of pine, fir, spruce and cedar have two balloons that facilitate their suspension in the air. Larch and Douglas-fir pollen grains are more or less spherical and without a balloon.

A pollen extract according to the invention may also contain an oily pollen extract, obtained from these same Pinaceae and/or Poaceae plants, containing liposoluble active ingredients obtained by extraction, for example a maceration, an infusion, a digestion, a decoction, a percolation or a leaching, preferably a maceration at room temperature between 15 and 27° C., of a vegetable raw material in an oily solvent such as an ether, for example diethyl ether, a ketone, for example acetone or an oil.

Preferably, the pollen extract according to the invention consists of an aqueous pollen extract obtained from a mixture of plants belonging to the Pinaceae and Poaceae family, that is to say it contains only an aqueous pollen extract and does not contain another pollen extract such as an oily extract.

According to the invention, aqueous extract means an extract containing water-soluble active ingredients obtained by extraction, for example a hydrodistillation, a maceration, an infusion, a digestion, a decoction, a percolation or even a leaching, preferably a maceration at low temperature between 15 and 40° C., of a vegetable raw material in an aqueous solvent, that is to say a solvent comprising water taken alone or advantageously mixed with other solvent(s) such as an alcohol, a ketone, and/or a non-ionic surfactant.

By way of non-limiting examples, the aqueous solvent is chosen from a mixture mainly comprising water in combination with an alcohol such as ethanol, a ketone such as acetone, and/or non-ionic surfactant.

The solvent can then be partially or totally removed to obtain an extract.

Preferably, the composition according to the invention used in the treatment and/or prevention of lower urinary tract symptoms (LUTS) in women comprises a pollen extract consisting of an aqueous pollen extract obtained from a plant mixture belonging to the Pinaceae and Poaceae family, an aqueous extract of plant seeds belonging to the genus *Cucurbita* and vitamin E or its esters.

The pollen extracts used in the composition according to the invention are preferably obtained from a mixture of plant(s) of the Poaceae family chosen from the genera *Secale, Zea* and/or *Dactylis* and of the Pinaceae family chosen from the genus *Pinus*.

More particularly, the aqueous pollen extract according to the invention is preferably obtained from a mixture of plant(s) of the Poaceae family chosen from the species *Secale cereale* L. (rye), *Zea mays* L. (maize), *Pinus sylvestris* L. (pine) and/or *Dactylis glomerata* L. (dactyl), and Pinaceae chosen from *Pinus sylvestris* L. (Scots pine) and/or *Pinus pinaster* (maritime pine).

The composition used according to the invention may further comprise an extract, aqueous and/or oily, preferably aqueous, of pistils obtained from these same plants.

Preferably, the plants used, from which the pollens and possibly pistils are obtained, are freshly harvested.

The pollens used for the present invention can be pollens collected by insects (such as bee pollen) or collected by human intervention. Bee pollen, for example, contains pollen, but also nectar and bee saliva. Pollen collected by human intervention is devoid of such additional ingredients. Preferably, said pollen of the present compositions are obtained only by human intervention. This once again allows a standardisation of the final product.

After their collection, the pollens and advantageously pistils can be used fresh or dried, advantageously dried, and optionally debacterised.

According to a preferred embodiment of the invention, the aqueous pollen extract is obtained from a mixture of:
an aqueous extract of pollen of *Secale cereale* L.;
an aqueous extract of pollen of *Zea mays* L.;
an aqueous extract of pollen of *Pinus sylvestris* L.;
an aqueous extract of pollen of *Dactylis glomerata* L.

Preferably, the composition used according to the invention further comprises an aqueous extract of the pistil of *Zea mays* L.

According to a particularly preferred embodiment of the invention, the aqueous pollen extract is obtained from a mixture of:
45% to 90% aqueous extract of pollen of *Secale cereale* L. by weight of the total weight of the extract;
1% to 35% aqueous extract of pollen of *Zea mays* L. by weight of the total weight of the extract;
0.01% to 5% aqueous extract of pollen of *Pinus sylvestris* L. by weight of the total weight of the extract;
3% to 30% aqueous extract of pollen of *Dactylis glomerata* L. by weight of the total weight of the extract.

Even more preferably, the composition used according to the invention further comprises 0.1% to 10% of aqueous extract of the pistil of *Zea mays* L. by weight of the total weight of the extract.

By way of non-limiting example of a process for preparing an aqueous extract of pollen, and advantageously of pistil, obtained from plant(s) belonging to the Pinaceae and/or Poaceae family, a process may be mentioned that comprises the successive stages of:
a) aqueous extraction of pollen;
b) aqueous extraction of pollen and advantageously of pistil;
c) spray drying the extracts obtained in steps a) and b); and
d) recovery of said extracts of pollen and pistil of plant(s) obtained in c).

The Applicant has been able to demonstrate that the extraction step was particularly sensitive. Thus, the temperature of the extraction must be strictly below 45° C. Beyond this temperature, one or more pollens and possibly pistils detailed above are no longer present. The quality of the composition and/or its efficacy are therefore not guaranteed.

Preferably, the temperature of the extraction should be less than 42° C.

The duration of the extraction step, for each of the extracts, is preferably at least 6 hours, preferably at least 10 hours, more preferably still at least 12 hours.

In addition, the Applicant has been able to demonstrate that excessive stirring degraded the extract(s). Thus, when the extraction is coupled with stirring, the latter should not exceed 6000 revolutions per minute (rpm), preferably 4500 rpm, more preferably 2800 rpm.

Preferably, the process for obtaining an aqueous extract of pollen, and advantageously of pistil, according to the invention comprises the following steps of:
a) extraction with water and/or a water-acetone mixture of pollens of *Secale cereale* L., *Zea mays* L., *Pinus sylvestris* L. and *Dactylis glomerata* L., at a temperature below 45° C. for at least 6 hours in order to obtain a first extract;
b) extraction with water and/or with a water-acetone mixture of pollens and advantageously pistil of *Zea mays* L. at a temperature below 45° C. for at least 6 hours in order to obtain a second extract;
c) mixture of the first and second extracts obtained in a) and b);
d) spray drying the mixture obtained in c); and
e) recovery of the mixture of extracts of pollen and advantageously of the pistil obtained in d).

The process thus developed makes it possible to guarantee good traceability of the pollens and pistils used.

The composition used according to the invention also comprises an aqueous extract of seeds of plant(s) belonging to the genus *Cucurbita*.

*Cucurbita* is a genus of climbing or creeping plants that belongs to the Cucurbitaceae family. It consists of 12 to 14 species, most of which are cultivated under the name of squash. The three main domesticated species are *Cucurbita pepo, Cucurbita maxima* and *Cucurbita moschata*.

The extract of seeds of plant(s) belonging to the genus *Cucurbita* used according to the invention is an aqueous extract containing fatty acids at a content of less than 10%, for example between 5 and 8%, by weight of the total weight of the extract.

Pumpkin seeds include in particular active substances known for their diuretic effect such as unsaturated fatty acids, sterols, vitamins and zinc.

Preferably, the composition used according to the invention comprises an aqueous extract of seeds of *Cucurbita pepo, Cucurbita maxima* and *Cucurbita moschata*, taken alone or as a mixture.

More preferably, the extract used in the composition according to the invention is an aqueous extract of pumpkin seeds (*Cucurbita pepo*).

After their collection, the seeds are advantageously dried, then optionally crushed.

According to a preferred embodiment of the invention, the aqueous extract of *Cucurbita* seeds is obtained from pumpkin seeds (*Cucurbita pepo*), dried then crushed and extracted by maceration at room temperature in water in a ratio ranging between 10:1 and 50:1, for example 20:1, 30:1 or 40:1.

Preferably, the aqueous extract of *Cucurbita* seeds used according to the invention is an extract of *Cucurbita pepo* containing fatty acids at a content of less than 10%, for example between 5 and 8%, by weight of the total weight of the extract. More preferably, the aqueous extract of *Cucurbita* seeds used according to the invention is an extract containing carbohydrates, fatty acids at a content of less than 10%, for example between 5 and 8%, proteins, fibres and sodium.

According to a particularly preferred embodiment, the aqueous extract of *Cucurbita pepo* seeds used according to the invention comprises 52% of carbohydrates, 6% of fatty acids, 24% of proteins, 14% of fibres, and 0.1%/0.25% of sodium/sodium chloride.

The composition used according to the invention also comprises vitamin E or its esters.

Vitamin E is a fat-soluble vitamin covering a set of eight organic molecules, four tocopherols ($\alpha$-tocopherol, $\beta$-tocopherol, $\gamma$-tocopherol and $\delta$-tocopherol) and four tocotrienols ($\alpha$-tocotrienol, $\beta$-tocotrienol, $\gamma$-tocotrienol and $\delta$-tocotrienol). The most biologically active form is $\alpha$-tocopherol. The most abundant form in the diet is $\gamma$-tocopherol. These molecules are present in large quantities in vegetable oils. They act, alongside vitamin C and glutathione, primarily as antioxidants against reactive oxygen derivatives.

Vitamin E esters refers to vitamin E chemically stabilised to avoid, for example, any oxidation problem. In this form, it has no antioxidant power. It is as it passes through the body that tocopheryls are hydrolysed and turn into tocopherols and become active. Examples of a vitamin E ester may include the acetate or succinate form, for example D-alpha-tocopheryl acetate.

Preferably, the composition used according to the invention comprises:
  5 to 40% by weight of the total weight of the composition of the aqueous pollen extract;
  20 to 80% by weight of the total weight of the composition of the aqueous extract of *Cucurbita* seeds; and
  0.1 to 10% by weight of the total weight of the composition of the vitamin E or its esters.
More preferably, the composition comprises:
  10 to 30% by weight of the total weight of the composition of the aqueous pollen extract, for example 10%, 15%, 20%, 25%, 30%;
  30 to 50% by weight of the total weight of the composition of the aqueous extract of *Cucurbita* seeds; for example 30%, 35%, 40%, 45%, 50%; and
  1 to 5% by weight of the total weight of the composition of the vitamin E or its esters, for example 1%, 2%, 3%, 4%, 5%.

The composition used according to the invention also comprises a physiologically acceptable medium proportioned to a reasonable benefit/risk ratio, comprising known excipients commonly used in herbal medicine such as binders, disintegrating agents, bulking agents, dispersing agents, agglomerating agents, lubricants, wetting agents, surfactants, emulsifiers, thickeners, flow agents, flavouring agents, sweetening agents, colouring agents, film-coating agents, stabilisers and/or preservatives advantageously not containing nanoparticles.

The person skilled in the art shall take care to choose these optional excipients and their quantity so that they do not harm the advantageous properties of the compositions used according to the invention.

Examples of excipients may include cellulose, preferably microcrystalline cellulose, and silicon dioxide.

In addition, advantageously, the composition used according to the invention can comprise another active agent chosen from manganese or alternatively extracts of *Betula alba, Cerasus avium, Equisetum arvense, Phaseolus vulgaris, Achillea millefolium, Agropyron repens, Galium verum, Lavandula officinalis, Mentha piperita*, and *Urticaria dioica*.

The addition of at least one of these other active agents, preferably manganese, will potentiate the effects of the composition used according to the invention.

The composition advantageously comprises 0.1 to 10% by weight of the total weight of the composition of one of these active elements taken alone or in combination, for example manganese.

The composition used according to the invention is preferably in a form suitable for oral administration, in one or more identical or different formulations. It is provided in any galenic form normally used for oral administration and in particular in the form of a capsule, tablet, liquid capsule, soft capsule, dragee, sachet, tube, vial, chewing gum, ball, emulsion, suspension, liquid, solution, ampoule, drink, syrup, powder, solid, soft gel, semi-solid.

Advantageously, the composition is formulated in the form of a tablet, capsule, soft capsule, soft gel, semi-solid, solid, liquid or powder.

Preferably, the daily dose of the composition used according to the present invention is between 360 mg and 1000 mg, preferably between 600 and 1000 mg, more preferably between 600 and 800 mg. This daily dose is preferably administered in 1, 2 or 3 doses (morning, noon and/or evening), for example in the form of 1, 2, 3, 4 or 6 tablets, preferably in one dose, more preferably during a period of at least 2 months, for example 2, 3 or 6 months, preferably 3 months.

The compositions according to the invention are used for the treatment and/or prevention of lower urinary tract symptoms (LUTS) associated with the filling, micturition and/or post-micturition phases in women, and more particularly of urinary incontinence.

The symptoms of the filling phase are the symptoms felt during the filling phase of the bladder without distinction between day and night. These are preferably the following symptoms:
  daytime pollakiuria, which is an increase in the frequency of urination during the day;
  nocturia, that is to say a need to urinate that wakes the patient. Nocturia must be differentiated from the "nocturnal micturition frequency" which corresponds to the totality of nocturnal micturition from the moment the patient goes to bed, but without taking into account the notion of awakening. The term "nocturnal pollakiuria" should be reserved for situations where it is desired to describe an abnormal increase in the frequency of nocturnal micturition and consequently introduces a notion of pathological threshold defined either by a number of events, or by a possible impact in terms of quality of life or discomfort;

urgency or micturition urgency is a sudden, compelling and frequently irrepressible desire to urinate. This term refers to the expression of a sudden, overwhelming urge to urinate, which is difficult or impossible to delay. It is a need that is abnormal in its brutality and intensity. It is often accompanied by only a moderate or even small amount of urine. It is different from the normal progression of need from a feeling of a full bladder to a feeling of wanting to urinate with a full bladder. The normal physiological need is the harbinger of urination which can be postponed for a certain time to satisfy social conveniences and environmental constraints;

urinary incontinence is an involuntary leakage of urine. The term urinary incontinence must be specified according to: the mechanism and circumstances of the occurrence of the leaks, their severity, their frequency, the existence of any contributing factors, their social, hygienic or quality of life impact, existence of any measures taken to avoid leaks and, finally, the notion of medical request from the patient;

stress urinary incontinence (SUI) is the involuntary leakage of urine during physical exertion, coughing and sneezing;

urinary incontinence due to urgency (or urge) is an involuntary leakage of urine accompanied or immediately preceded by urgency;

mixed urinary incontinence (MUI) is an involuntary leakage of urine associated with urgency with, also, involuntary leakage of urine during exercise, coughing or sneezing;

overflow incontinence is a leak due to the fact that the person is unable to empty their bladder completely. This results in frequent and often repeated leaks of urine;

enuresis is involuntary urination. The term nocturnal enuresis describes enuresis that occurs during sleep;

permanent incontinence is a permanent urine leak;

bladder sensitivity:

normal: the patient describes a gradually increasing need to urinate until they feel an urgent need;

increased: the patient describes a very early and persistent need to urinate;

reduced: the patient feels the increase in bladder volume but does not feel the need to urinate;

absent: the patient does not feel any sensation.

The different symptoms related to the micturition phase are:

weakness of the stream: the patient's perception of a decrease in the force of the urine stream during urination;

stream like a watering can;

intermittent stream: urination interrupted one or more times;

hesitant stream: delay in initiating micturition;

urination by thrust: urinary stream obtained with a concomitant abdominal thrust;

terminal drops, dragging urination: gradual and slow completion of urination which ends in a drip flow.

Symptoms of the post-micturition phase are the symptoms experienced by the patient immediately after the end of micturition:

feeling of incomplete bladder emptying is a subjective feeling that the bladder has not emptied completely after micturition;

delayed drops are involuntary urine loss that occurs immediately after micturition, most often when leaving the toilet for a man or when getting up from the toilet for a woman.

Dyspareunia, vaginal dryness and urinary incontinence are the main symptoms described during sexual intercourse and can also be treated with the compositions used according to the invention.

Many symptoms can be expressed by patients, due to urogenital prolapse, for example: feeling of pelvic heaviness or endovaginal foreign body, need to push back a vaginal mass in order to be able to urinate or have a bowel movement, and can also be treated.

The sensation of pain to be treated with the compositions according to the invention can be characterised as to its frequency of occurrence, its intensity, its duration, the existence of any contributing factors or its location, such as:

cystalgia, which is a general term to define pain felt in the pre- or retro-pubic region. The pain usually increases with bladder filling and may eventually persist after micturition. This term should be preferred to that of "interstitial cystitis", which corresponds to a pathological entity defined more precisely according to a set of diagnostic criteria;

urethralgia, which is pain felt in the urethra and to which the patient refers;

vulvar pain, which is pain felt strictly at the vulvar level;

vaginal pain, which is pain felt inside the vaginal cavity beyond the vulvar segment;

scrotal pain, the description of which does not suggest a more specific location in the cord, testis, epididymis, or even skin;

perineal pain, which is a pain felt, in women, between the vulvar fork and the anus and, in men, between the scrotum and the anus;

pelvic pain, which is pain less clearly defined in terms of its precise location, more diffuse and not directly related to the cycle of filling-micturition of the bladder.

Preferably, the compositions according to the invention are used in the treatment and/or prevention of urinary incontinence in women. They are more particularly used for the treatment and/or prevention of stress urinary incontinence (SUI), urinary incontinence due to urgency (or urge), mixed urinary incontinence (MUI), urinary incontinence by overflow, enuresis and/or permanent incontinence, even more preferably for the treatment and/or prevention of stress urinary incontinence (SUI), urinary incontinence by urgency (or urge) and mixed urinary incontinence (MUI), including in particular the reduction in the frequency of nocturnal micturition inducing an awakening.

More preferably, the compositions according to the invention comprising a pollen extract consisting of an aqueous pollen extract obtained from a plant mixture belonging to the Pinaceae and Poaceae family, an aqueous extract of the pistil of *Zea mays* L., an aqueous extract of plant seeds belonging to the genus *Cucurbita* and vitamin E or its esters are used in the treatment of urinary incontinence, in particular stress urinary incontinence (SUI), the urinary incontinence due to urgency (or urge) and mixed urinary incontinence (MUI), including in particular the reduction in the frequency of nocturnal micturition inducing an awakening.

It is known that the functions of the lower urinary tract, to periodically store and evacuate urine, depend on the activity of smooth and striated muscles in the bladder, urethra and the external sphincter of the urethra.

While urine is stored, the outlet is closed and the smooth muscle of the bladder is at rest. When the bladder volume reaches the micturition threshold, activation of a pontine micturition activating centre induces bladder contraction and reciprocal urethral relaxation, resulting in emptying of the bladder.

During emptying, the parasympathetic sacral (pelvic) nerves exert an excitatory (cholinergic and purinergic) action on the bladder via the pelvic nerves and an inhibitory (nitrergic) action on the urethra. These peripheral systems are integrated by excitatory and inhibitory regulation in the spinal cord and brain. Injury or disease of the nervous system, as well as pharmaceuticals and peripheral organ disorders, can cause lower urinary tract dysfunction.

In the case of an overactive bladder (OAB), therapeutic targets to facilitate urine storage can be found in the urothelium, detrusor muscle, autonomic and afferent pathways, spinal cord and brain.

Urothelium appears to have specialised sensory and signalling properties, including: (1) expression of nicotinic, muscarinic, tachykinin, adrenergic, bradykinin and transient receptor potential (TRP) receptors, (2) a close physical association with afferent nerves, and (3) the ability to release chemical molecules such as adenosine triphosphate (ATP), acetylcholine, and nitric oxide.

The increased expression and/or sensitivity to those urothelial sensory molecules which lead to afferent sensitivity may be responsible for OAB.

Targeting the afferent pathways and/or smooth muscles of the bladder by modulating the activity of receptors (e.g. neurokinin, ATP or β3-adrenergic) and ion channels (e.g. TRPV1 or K) could be effective in suppressing OAB.

In the case of stress urinary incontinence (stress), pharmaceutical therapies targeting the neuron-mediated urethral continence reflex during stress conditions such as sneezing or coughing may be effective in increasing output resistance. Therapeutic targets include adrenergic and serotonergic receptors in the spinal cord as well as adrenergic receptors in the urethral sphincter, which may respectively enhance urethral reflex activity during stressful conditions and increase baseline urethral pressure.

Thus, the compositions according to the invention used in the treatment and/or prevention of urinary incontinence could have an action at the level of the nervous system, in particular of the afferent pathways and of the smooth muscle, by acting for example on one or more of these molecular targets in the urothelium, urethra and bladder.

The compositions are also used for the treatment and/or prevention of genitourinary pain syndromes and clinical syndromes suggestive of dysfunction of the lower urinary tract.

Syndromes are associations of different symptoms, but they are not necessarily pathognomonic of a medical condition. The term "syndrome" can only be used if there are a plurality of symptoms in the same patient. The various syndromes treated correspond to functional abnormalities for which no specific cause has been identified, it being understood that the usual means of investigation have eliminated an obvious local organic pathology such as, for example, infection, tumour, or hydroelectrolytic disorder.

Genitourinary pain syndromes are all chronic in nature. Pain, which is the predominant complaint, can be associated with other symptoms concerning the lower urinary tract, the genito-sexual sphere or the digestive tract:

bladder pain syndrome is increased supra pubic pain during bladder filling, associated with daytime or nocturnal pollakiuria in the absence of urinary tract infection or bladder tissue pathology;

urethral pain syndrome is recurrent urethral pain occurring preferentially during micturition in the absence of urinary tract infection or bladder tissue pathology;

vulvar pain syndrome is permanent or intermittent vulvar pain which may vary depending on the micturition cycle or be associated with symptoms suggestive of lower urinary tract dysfunction or sexual disorders;

vaginal pain syndrome is permanent or intermittent vaginal pain associated with symptoms suggestive of lower urinary tract dysfunction or sexual disturbances, in the absence of proven vaginal infection or any other obvious vaginal pathology;

scrotal pain syndrome is permanent or intermittent scrotal pain associated with symptoms suggestive of lower urinary tract dysfunction or sexual disorders, in the absence of epididymitis or any other local pathology;

perineal pain syndrome is permanent or intermittent perineal pain associated with symptoms suggestive of lower urinary tract dysfunction or sexual disorders, in the absence of proven infection or any other obvious perineal pathology;

pelvic pain syndrome is permanent or intermittent pelvic pain associated with symptoms suggestive of dysfunction of the lower urinary tract, digestive system or sexual disorders, in the absence of proven infection or any other obvious pathological condition.

In clinical practice, an empirical diagnostic approach is frequently used to decide how to manage a patient with symptoms suggestive of lower urinary tract dysfunction:

"clinical overactive bladder syndrome" or "urgency-pollakiuria syndrome" is defined by the occurrence of urgency with or without urinary incontinence, usually associated with pollakiuria or nocturia. This syndrome is suggestive of detrusor hyperactivity evidenced by a urodynamic examination, but not specific because it may also be due to other types of dysfunction of the lower urinary tract. Furthermore, the term "clinical syndrome of overactive bladder" assumes that there is no urinary tract infection or obvious local organic pathology (tumour, etc.);

"dysuric syndrome" suggestive of sub-bladder obstruction should be used in a man with predominantly micturition-related disorders, and in the absence of urinary tract infection or obvious local pathology. In women, dysuric syndrome should suggest an overactive bladder rather than a sub-bladder obstruction.

EXAMPLES

The present invention will now be illustrated with the following examples.

Example 1: Tablet (Table 1)

| Ingredients | Quantity in mg/tablet |
| --- | --- |
| Aqueous extract of pollen containing by weight of the total weight of the extract: 70-75% of *Secale cereale* L. pollen 15-20% of *Zea mays* L. pollen 0.05-1.0% of *Pinus sylvestris* L. pollen 5-10% of *Dactylis glomerata* L. pollen and 1-4% of an aqueous extract from the pistil of *Zea mays* L. | 120-200 |
| Aqueous extract of *Cucurbita* seeds containing less than 10% fatty acids | 200-400 |

-continued

| Ingredients | Quantity in mg/tablet |
|---|---|
| Esters of vitamin E | 16-30 |
| Microcrystalline cellulose | 100-300 |
| Silicon dioxide | 1-10 |
| Anti-caking agent | 100-400 |

Example 2: Capsule (Table 2)

| Ingredients | Quantity in mg/capsule |
|---|---|
| Aqueous extract of pollen containing by weight of the total weight of the extract: 70-75% of *Secale cereale* L. pollen 15-20% of *Zea mays* L. pollen 0.05-1.00 of *Pinus sylvestris* L. pollen 5-10% of *Dactylis glomerata* L. pollen and advantageously 0.6-2% of an aqueous extract from the pistil of *Zea mays* L. | 120-200 |
| Aqueous extract of *Cucurbita* seeds containing less than 10% fatty acids | 100-200 |
| Esters of vitamin E | 8-20 |
| Microcrystalline cellulose | 100-300 |
| Silicon dioxide | 1-10 |
| Lubricant | 1-5 |
| Anti-caking agent | 100-400 |

Example 3: Soft Capsule (Table 3)

| Ingredients | Quantity in mg/capsule |
|---|---|
| Aqueous extract of pollen containing by weight of the total weight of the extract: 70-75% of *Secale cereale* L. pollen 15-20% of *Zea mays* L. pollen 0.05-1.00 of *Pinus sylvestris* L. pollen 5-10% of *Dactylis glomerata* L. pollen and advantageously 1-4% of an aqueous extract from the pistil of *Zea mays* L. | 120-200 |
| Aqueous extract of *Cucurbita* seeds containing less than 10% fatty acids | 200-400 |
| Esters of vitamin E | 16-30 |
| Vegetable oil | 100-500 |

Example 4: Capsule (Table 4)

| Ingredients | Quantity in mg/capsule |
|---|---|
| Aqueous extract of pollen containing by weight of the total weight of the extract: 70-75% of *Secale cereale* L. pollen 15-20% of *Zea mays* L. pollen 0.05-1.00 of *Pinus sylvestris* L. pollen 5-10% of *Dactylis glomerata* L. pollen and advantageously 0.6-4% of an aqueous extract from the pistil of *Zea mays* L. | 200-400 |
| Aqueous extract of *Cucurbita* seeds containing less than 10% fatty acids | 100-200 |
| Esters of vitamin E | 8-20 |
| Microcrystalline cellulose | 100-300 |
| Silicon dioxide | 1-10 |
| Lubricant | 1-5 |
| Anti-caking agent | 100-400 |

The compositions according to the invention comprising a pollen extract containing (and preferably consisting of) an aqueous pollen extract, an aqueous extract of *Cucurbita* seeds containing less than 10% fatty acids and vitamin E or its esters, and advantageously, in addition, an aqueous extract of the pistil of *Zea mays* L, are formulated according to techniques commonly known and used by the person skilled in the art.

Example 5: Activity Study on Urinary Incontinence in Women

A study was carried out on 160 patients aged between 18 and 75 years (60.35 mean age) suffering from LUTS, and more specifically from urinary incontinence.

The study dropout rate was 21.875%, due to causes such as GP advice, change in treatment, side effects, and lack of specific cause and loss of follow-up (9 patients).

Among the patients who participated in the study, treatment adherence was very satisfactory; the tablets were taken at the correct time and in the correct form.

The results were obtained after administration once a day for at least 2 months (and up to 3 months) with composition C (composition according to Example 1) and compared with the administration under the same conditions of either:
- a composition A comprising 120-200 mg of an aqueous extract of P2 pollen and 5-10 mg of an oily extract of EA5 pollen (=GRAMINEX®), 100-300 mg of an aqueous extract of pumpkin seeds and 16-30 mg of D-alpha-tocopheryl acetate;
- a composition B comprising 120-200 mg of an aqueous extract of P2 pollen and 5-10 mg of an oily extract of EA5 pollen (=GRAMINEK®); or
- a placebo (tablet comprising microcrystalline cellulose, isomalt, magnesium stearate, silicon dioxide, and a coating agent (Aqua Polish D Grey 089.45 MS)).

The efficacy of the different compositions was evaluated with validated questionnaires, namely the SANDVIK, MUH (Measurement of Urinary Handicap) and ICIQ (International Consultation on Incontinence Questionnaire) scales.

The severity score developed by SANDVIK (Incontinence Severity Index; Sandvik H, Hundskaar S et al. Validation of a severity index in female urinary incontinence and its implementation in an epidemiological survey. J Epidemiol Community Health 1993; 47: 497-99) enables the severity of incontinence to be classified into four stages (minimal, moderate, severe, very severe).

The MUH (Measurement of Urinary Handicap) scale published by Amarenco in 1992 (Amarenco G, Kerdraon J, Perrigot M. Pelvic handicap evaluation scale: measurement of urinary handicap (MUH). In: Rééducation vésicosphinctérienne et anorectale. Edited by Pelissier J, Costa P, Lopez S, Mares P, Masson Ed, 1992, 498-504) makes it possible to obtain quantitative measurements of various urinary symptoms. This questionnaire can be used regardless of the type of urinary incontinence. It has 7 questions with a response scale of 0 to 4. It has been modified for female non-neurological urinary incontinence by removing the question on "other incontinence" and replacing it with a question on the frequency of stress incontinence. It results in a score of 0 to 28 with four sub-scores: urgency (0 to 8), stress (0 to 8), pollakiuria (0 to 8) and dysuria (0 to 4).

The ICIQ scale (International Consultation on Incontinence Questionnaire; Avery K, Donovan J, Peters T J et al. (2004) International Consultation on Incontinence Questionnaire (ICIQ): a brief and robust measure for evaluating the symptoms and impact of urinary incontinence. Neurourol Urodyn 2004; 23: 322-30.) is one of the most recent questionnaires developed for women to assess urinary incontinence (stress, urgency or mixed). It has only four items. Of these, three assess incontinence as a symptom (frequency, volume and circumstances of leakage), with the fourth item measuring the impact on quality of life as a visual analogue scale.

In particular, the results obtained before treatment (D0), after 60 days of treatment (D60) and after 90 days of treatment (D90) were measured with these different scales and are compiled in Table 5 below. The results thus obtained are also illustrated in FIGS. 1 to 3.

Figure 2:
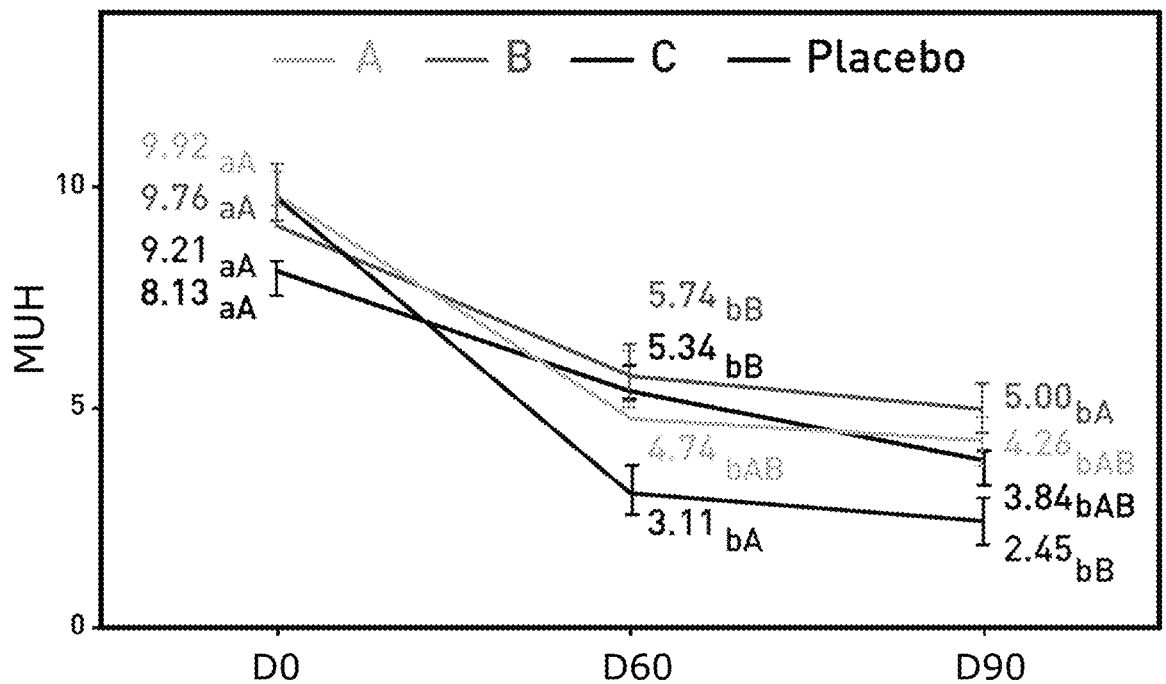
FIG. 2 shows the results obtained with the MUH scale (Measurement of Urinary Handicap) in a comparative manner with different compositions in the context of the study according to Example 5 on urinary incontinence in women before treatment (D0), after 60 days of treatment (D60) and after 90 days of treatment (D90).
Figure 3:
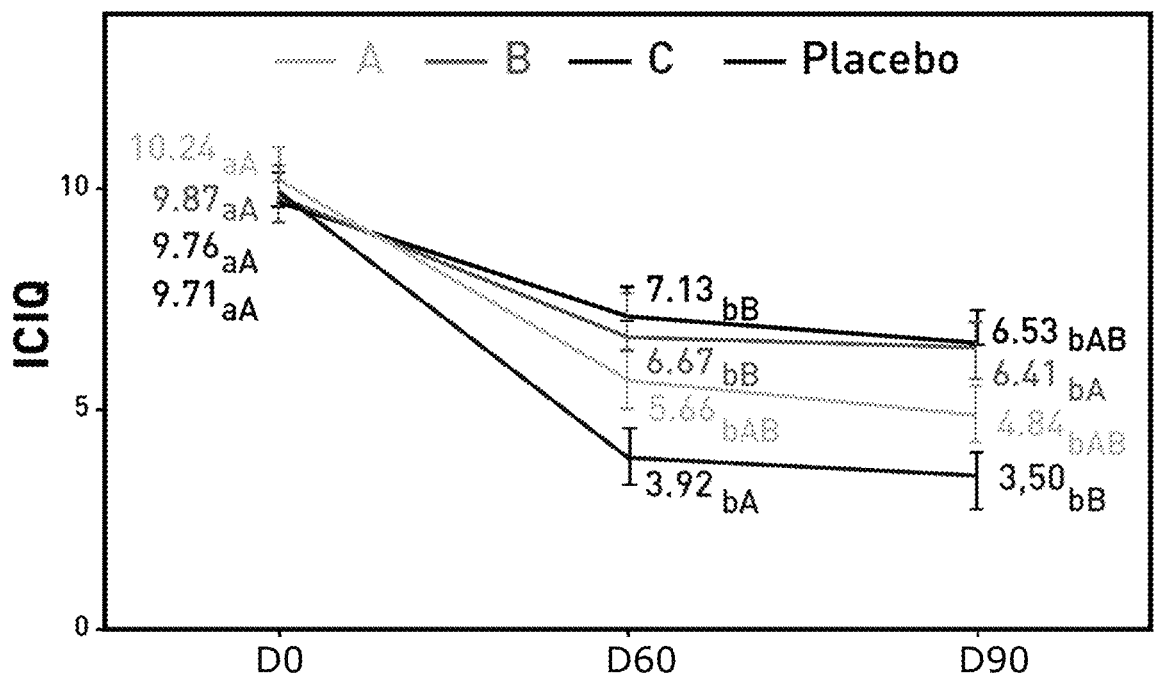
FIG. 3 shows the results obtained with the ICIQ scale (International Consultation on Incontinence Questionnaire) in a comparative manner with different compositions in the context of the study according to Example 5 on urinary incontinence in women before treatment (D0), after 60 days of treatment (D60) and after 90 days of treatment (D90).

In these FIGS. 1 to 3 as well as in FIGS. 4 to 9, the following references are mentioned:
- a-c. Two-by-two comparisons. Within the same group, different lower-case letters indicate statistically significant differences between each time (Bonferroni correction).
- A-B. Two-by-two comparisons. For the same given time, different capital letters indicate statistically significant differences between the groups (Bonferroni correction).

TABLE 5

| Time | Average (standard deviation) 0 months | | Average (standard deviation) 2 months | | Average (standard deviation) 3 months | |
|---|---|---|---|---|---|---|
| TOTAL SCORE SANDVIK | | | | | | |
| A | 6.35 | 2.36 | 3.68 | 1.94 | 2.87 | 2.64 |
| Placebo | 5.91 | 2.14 | 4.03 | 2.5 | 3.53 | 2.73 |
| B | 5.91 | 2.78 | 3.66 | 2.87 | 3.06 | 2.96 |
| Placebo | 5.91 | 2.14 | 4.03 | 2.5 | 3.53 | 2.73 |
| C | 6.08 | 2.32 | 3.25 | 2.88 | 2.33 | 2.3 |
| Placebo | 5.91 | 2.14 | 4.03 | 2.5 | 3.53 | 2.73 |
| TOTAL SCORE MUH | | | | | | |
| A | 9.92 | 3.73 | 4.74 | 3.49 | 4.26 | 3.7 |
| Placebo | 8.13 | 3.48 | 5.34 | 3.34 | 3.84 | 3.15 |
| B | 9.21 | 3.54 | 5.74 | 3.82 | 5 | 3.89 |
| Placebo | 8.13 | 3.48 | 5.34 | 3.34 | 3.84 | 3.15 |
| C | 9.76 | 4.04 | 3.11 | 3.81 | 2.45 | 3.19 |
| Placebo | 8.13 | 3.48 | 5.34 | 3.34 | 3.84 | 3.15 |
| TOTAL SCORE ICIQ | | | | | | |
| A | 10.24 | 3.92 | 5.66 | 3.77 | 4.84 | 3.57 |
| Placebo | 9.71 | 3.14 | 7.13 | 4.11 | 6.53 | 4.71 |
| B | 9.87 | 4.77 | 6.67 | 4.13 | 6.41 | 4.98 |
| Placebo | 9.71 | 3.14 | 7.13 | 4.11 | 6.53 | 4.71 |
| C | 9.76 | 4.56 | 3.92 | 4.44 | 3.5 | 3.81 |
| Placebo | 9.71 | 3.14 | 7.13 | 4.11 | 6.53 | 4.71 |

The results of the study with the three questionnaires analysed (SANDVIK, MUH and ICIQ) show that the three groups of patients who received compositions A, B or C respectively showed a statistically significant improvement compared to the placebo group.

Among the three compositions administered, it appears that composition C (according to Example 1 according to the invention) is that which brought the most improvement in the patients, followed by the treatment group with composition A then finally with the composition B.

For example, after 60 days of treatment with composition C according to the invention, an average decrease in the urinary severity and/or symptoms of the order of 46.55% (SANDVIK score), 68.14% (MUH score) and 59.44% (ICIQ score) was evident in the treated patients.

By comparison, the average decreases obtained respectively with compositions A and B are only 42.05% and 38.07% (SANDVIK scores), 52.22% and 37.68% (MUH scores) and 44.73% and 32.42% (ICIQ scores).

After 90 days of treatment, the average decreases with composition C according to the invention are respectively 61.68% (SANDVIK), 74.9% (MUH) and 64.14% (ICIQ).

By comparison, the average decreases obtained respectively with compositions A and B are only 54.8% and 48.22% (SANDVIK scores), 57.07% and 45.71% (MUH scores) and 52.73% and 35.06% (ICIQ scores).

These results are consistent with the decrease in the severity of urinary incontinence, initially classified as very severe, severe and moderate and defined at the end of treatment with a significant percentage of mild cases and even of patients who are no longer incontinent and are fully recovered.

These results demonstrate the effectiveness of the treatment, more particularly with composition C (Example 1 according to the invention), with maximum effectiveness at 60 days, the positive effect being maintained 90 days after the start (during the last visit).

Figure 4:
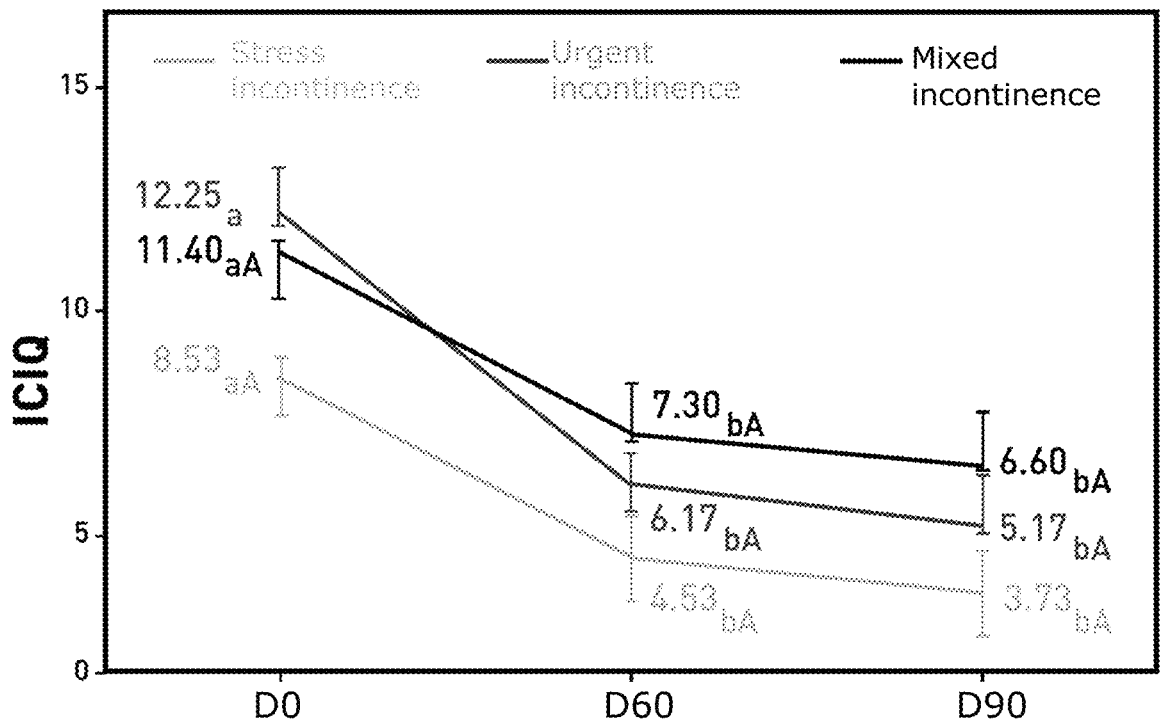
FIG. 4 shows the results obtained by type of incontinence with the ICIQ scale with composition A in the context of the study according to Example 5 on urinary incontinence in women before treatment (D0), after 60 days of treatment (D60) and after 90 days of treatment (D90).
Figure 5:
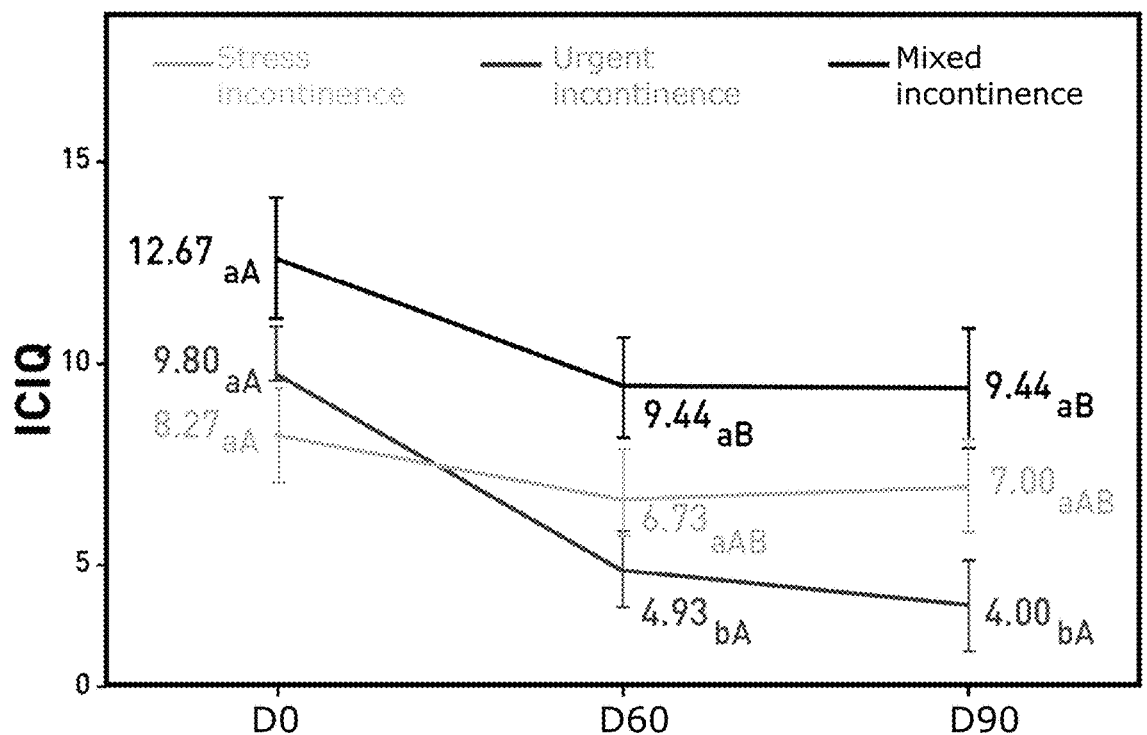
FIG. 5 shows the results obtained by type of incontinence with the ICIQ scale with composition B in the context of the study according to Example 5 on urinary incontinence in women before treatment (D0), after 60 days of treatment (D60) and after 90 days of treatment (D90).
Figure 6:
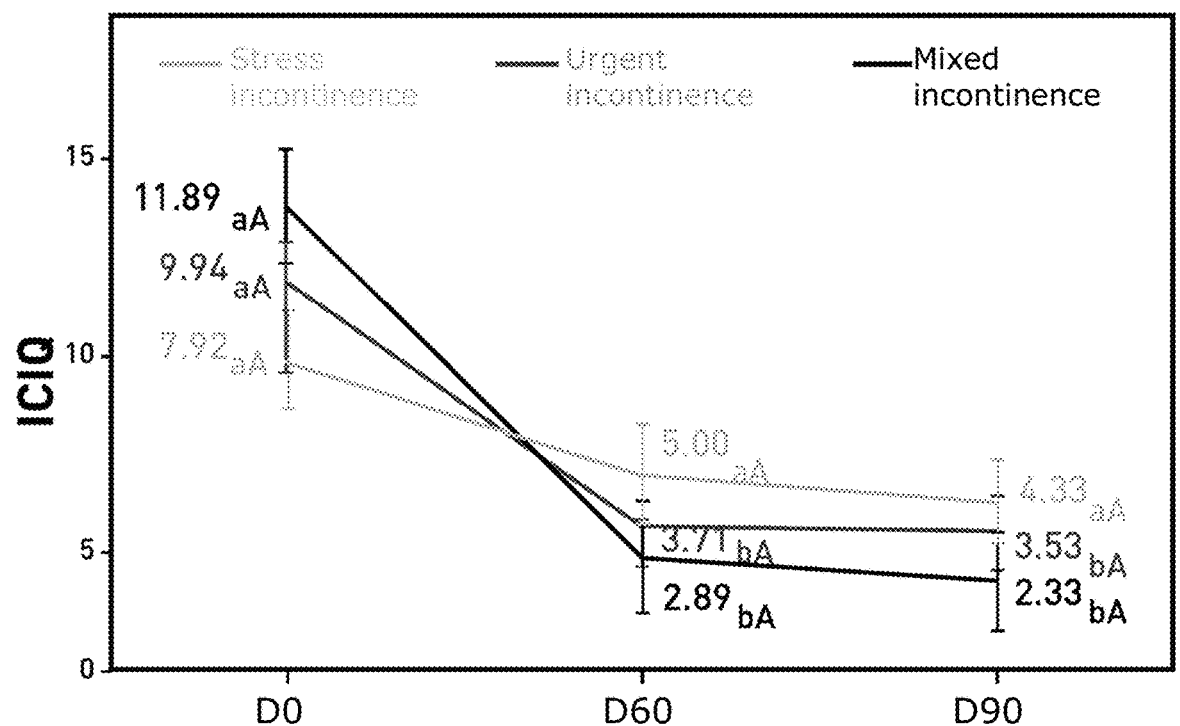
FIG. 6 shows the results obtained by type of incontinence with the ICIQ scale with composition C in the context of the study according to Example 5 on urinary incontinence in women before treatment (D0), after 60 days of treatment (D60) and after 90 days of treatment (D90).
Figure 7:
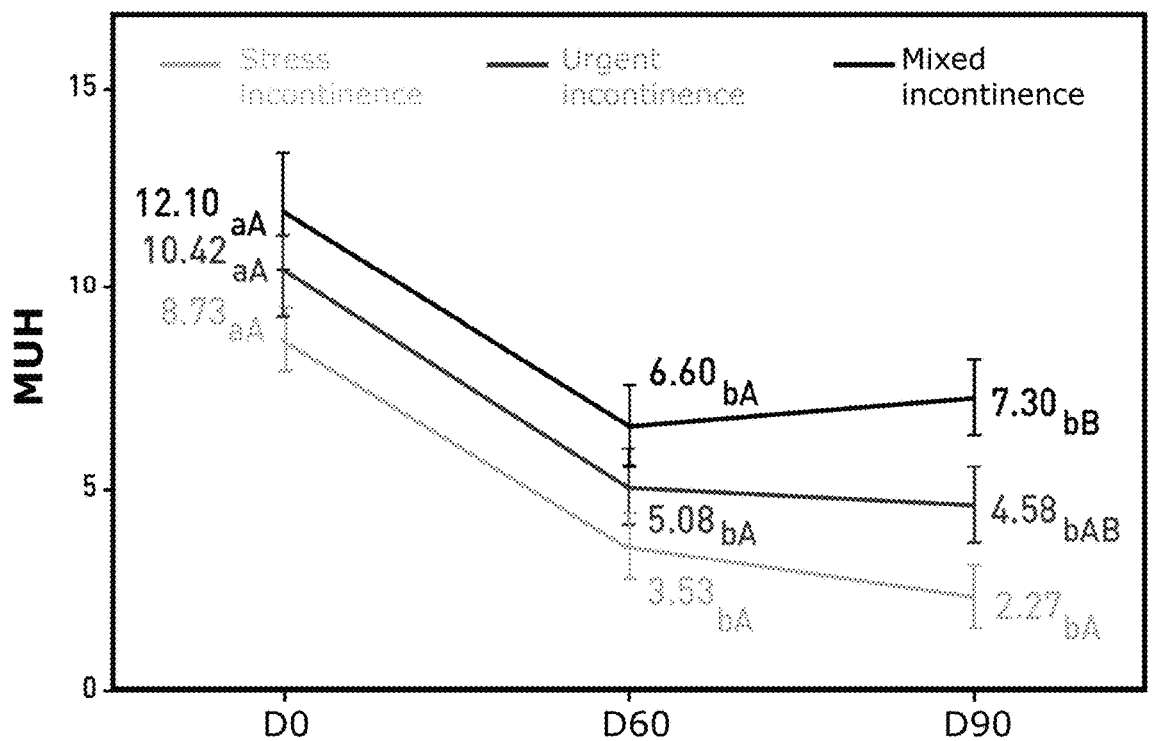
FIG. 7 shows the results obtained by type of incontinence with the MUH scale with composition A in the context of the study according to Example 5 on urinary incontinence in women before treatment (D0), after 60 days of treatment (D60) and after 90 days of treatment (D90).
Figure 8:
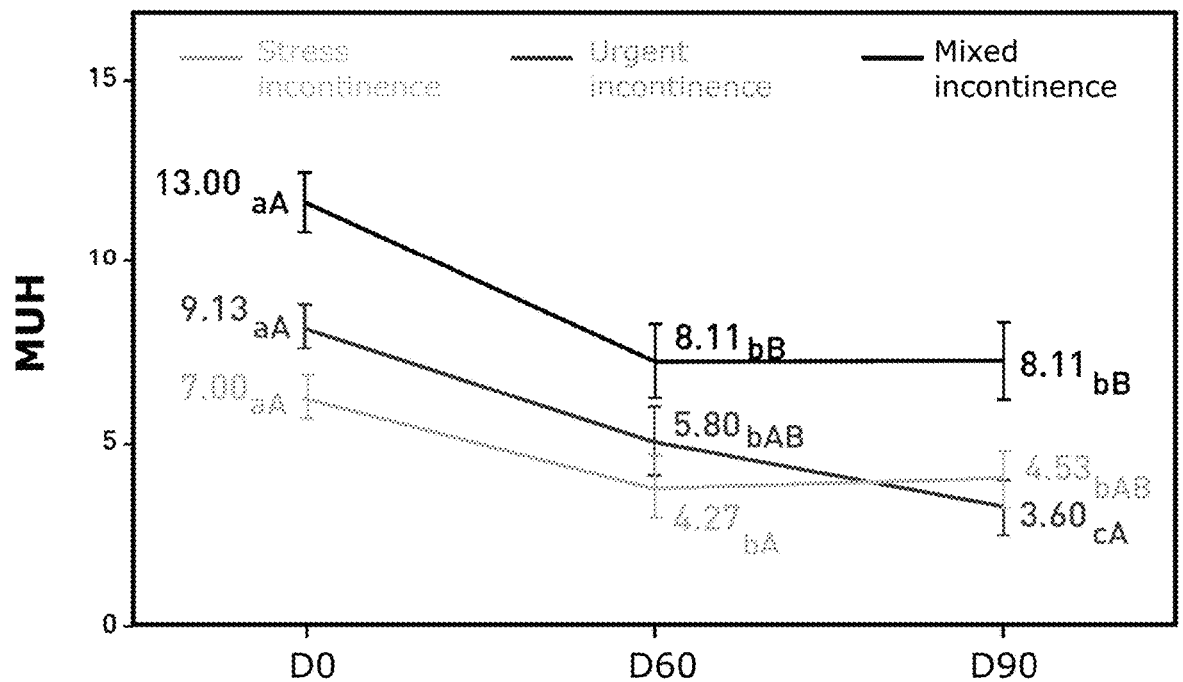
FIG. 8 shows the results obtained by type of incontinence with the MUH scale with composition B in the context of the study according to Example 5 on urinary incontinence in women before treatment (D0), after 60 days of treatment (D60) and after 90 days of treatment (D90).
Figure 9:
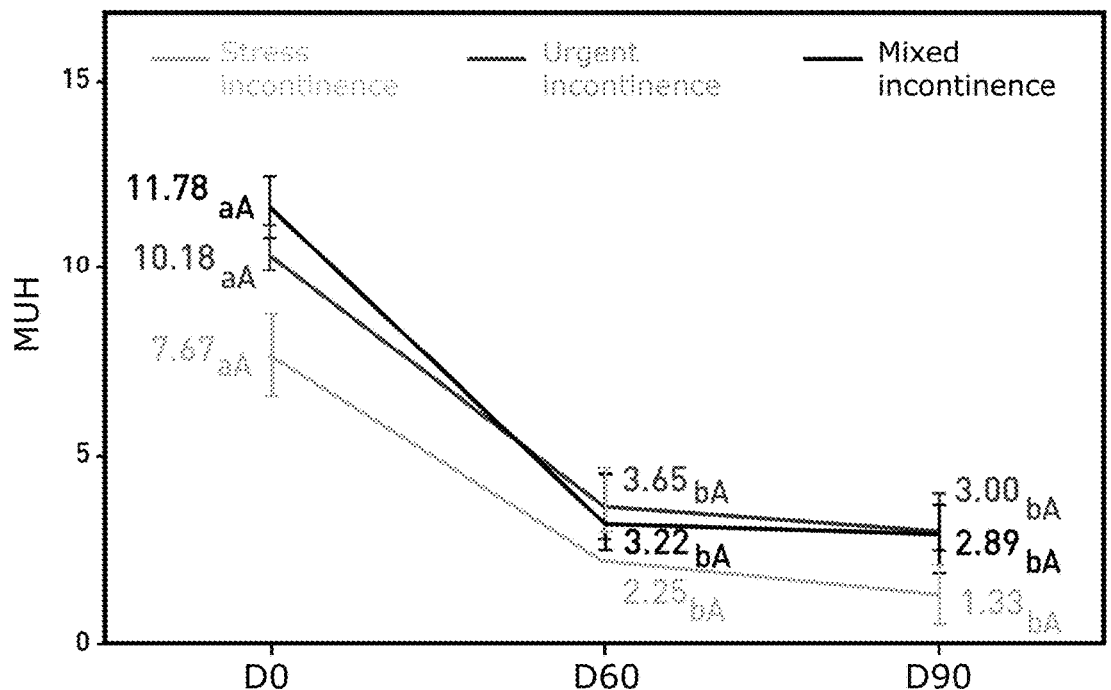
FIG. 9 shows the results obtained by type of incontinence with the MUH scale with composition C in the context of the study according to Example 5 on urinary incontinence in women before treatment (D0), after 60 days of treatment (D60) and after 90 days of treatment (D90).
Figure 10:
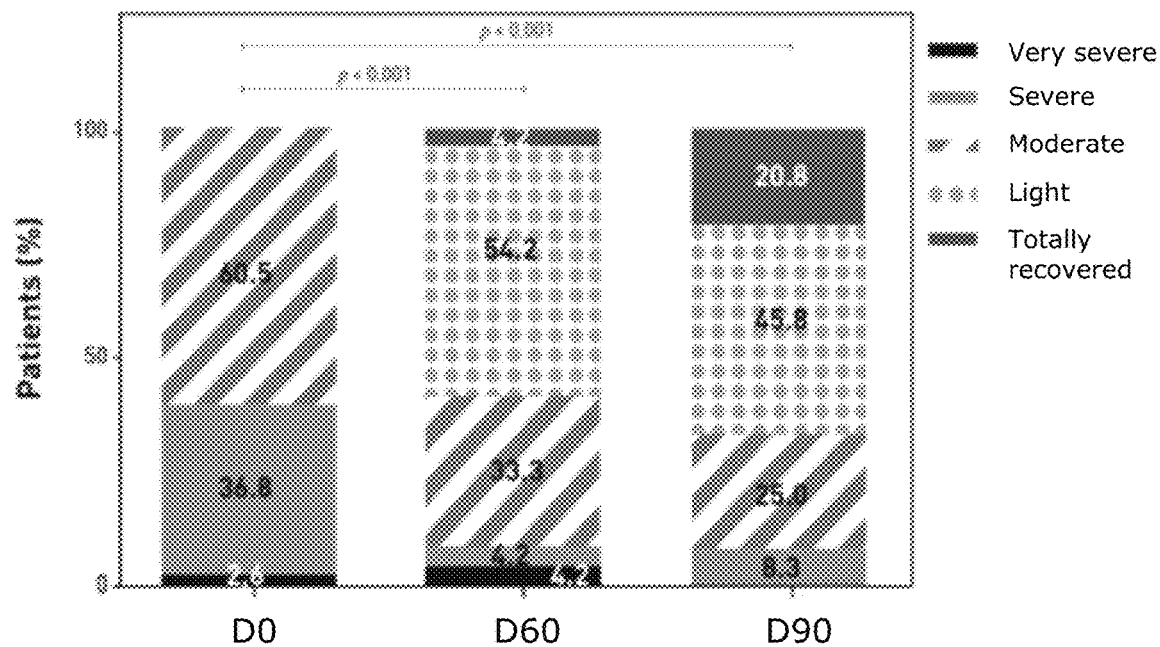
FIG. 10 shows the results obtained with the SANDVIK scale with composition C in the context of the study according to Example 5 on any type of urinary incontinence combined in women before treatment (D0), after 60 days of treatment (D60) and after 90 days of treatment (D90).

More particularly, the results obtained by type of incontinence for each of the compositions A to C tested are respectively illustrated by FIGS. 4 to 6 with the ICIQ scale, by FIGS. 7 to 9 with the MUH scale and by FIG. 10 with the SANDVIK scale for composition C according to the invention.

According to the results obtained, according to an advantageous embodiment of the invention, urinary incontinence due to urgency (or urge) and mixed urinary incontinence are more particularly statistically significantly improved at 60 days.

For example, as illustrated in FIG. 6, after 60 days of treatment with composition C according to the invention, an average decrease in the severity and/or urinary symptoms is noted with the ICIQ score of 36.87% for stress urinary incontinence, 62.68% for urge urinary incontinence and 75.69% for mixed urinary incontinence, the scores being respectively 40.28%, 64.49% and 80.4% after 90 days of treatment.

Likewise, as illustrated in FIG. 9, after 60 days of treatment with composition C according to the invention, an average decrease in the urinary severity and/or symptoms is noted with the MUH score of 70.66% for stress urinary incontinence, 64.15% for urge urinary incontinence and 72.67% for mixed urinary incontinence, the scores being respectively 82.66%, 70.53% and 75.47% after 90 days of treatment.

Finally, as illustrated in FIG. 10, from the score obtained with the SANDVIK scale, a significant improvement in the severity of urinary incontinence can be observed in the patients treated with composition C according to the invention: for example, we go from 39.4% for very severe (2.6%) and severe (36.8%) cases to only 8.4% (4.2%+4.2%) on D60 with the appearance of 54.2% of mild cases and even 4.2% of fully recovered patients, or even 45.8% (mild) and 20.8% (fully recovered), respectively, on D90.

Example 6: Safety and Efficacy Study of a Composition According to the Invention in Women with Urinary Incontinence Due to Urgency (or Urge) or Mixed Urinary Incontinence (Randomised, Double-Blind, Placebo-Controlled Clinical Trial)

The aim of this study is to identify the response of a composition according to the invention in women diagnosed with symptoms of overactive bladder (OAB) presenting urinary incontinence due to urgency (or urge) or mixed urinary incontinence.

In this study, 52 women were divided into two groups. One was treated with the composition according to the invention (according to Example 1=PSCEP in FIGS. 11-13) (n=26) and one was treated with placebo (n=26). Efficacy was assessed using validated questionnaires, namely the SANDVIK, MUH (Measurement of Urinary Handicap) and ICIQ-UI SF (International Consultation on Incontinence Questionnaire-Urinary Incontinence Short Form) scales.

No side effects were observed in any of the groups.

Results

There was no difference at the outset in terms of demographic characteristics and incontinence between the 2 groups.

Figure 11:
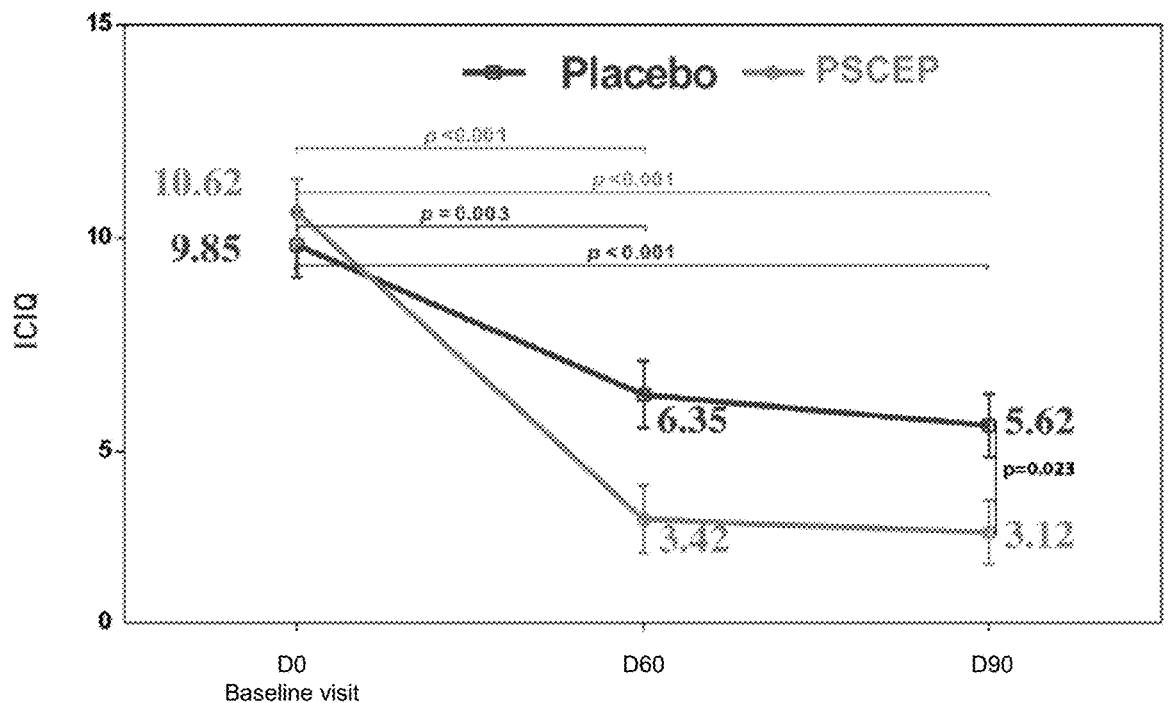
FIG. 11 shows the results obtained with the ICIQ scale in the context of Example 6 on the efficacy of a composition according to the invention (according to Example 1=PSCEP; versus placebo) in women with urinary urgency (or urge) incontinence or mixed urinary incontinence before treatment (D0), after 60 days of treatment (D60) and after 90 days of treatment (D90).

As illustrated by FIG. 11, after 90 days, with the ICIQ-UI SF, a significant improvement was observed in the group treated with the composition according to the invention "PSCEP" (p<0.001) compared to the baseline and in comparison with the placebo group, a significant improvement was also shown (p=0.023).

Figure 12:
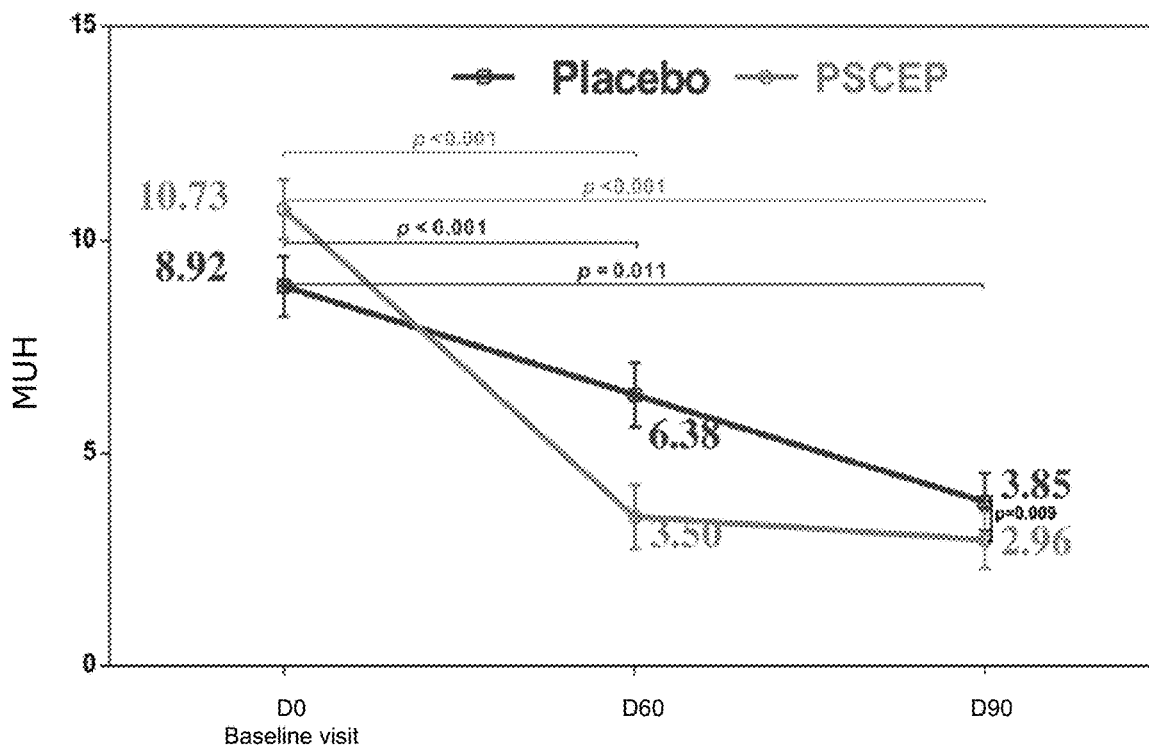
FIG. 12 shows the results obtained with the MUH scale in the context of Example 6 on the efficacy of a composition according to the invention (according to Example 1=PSCEP; versus placebo) in women with urinary urgency (or urge) incontinence or mixed urinary incontinence before treatment (D0), after 60 days of treatment (D60) and after 90 days of treatment (D90).

As shown in FIG. 12, with MUH, a significant improvement was shown in the group treated with the composition according to the invention "PSCEP" (p<0.001) compared to the baseline. Compared with the placebo group, a significant improvement after 90 days (p=0.009) was observed in the women treated with the composition according to the invention "PSCEP".

Figure 13:
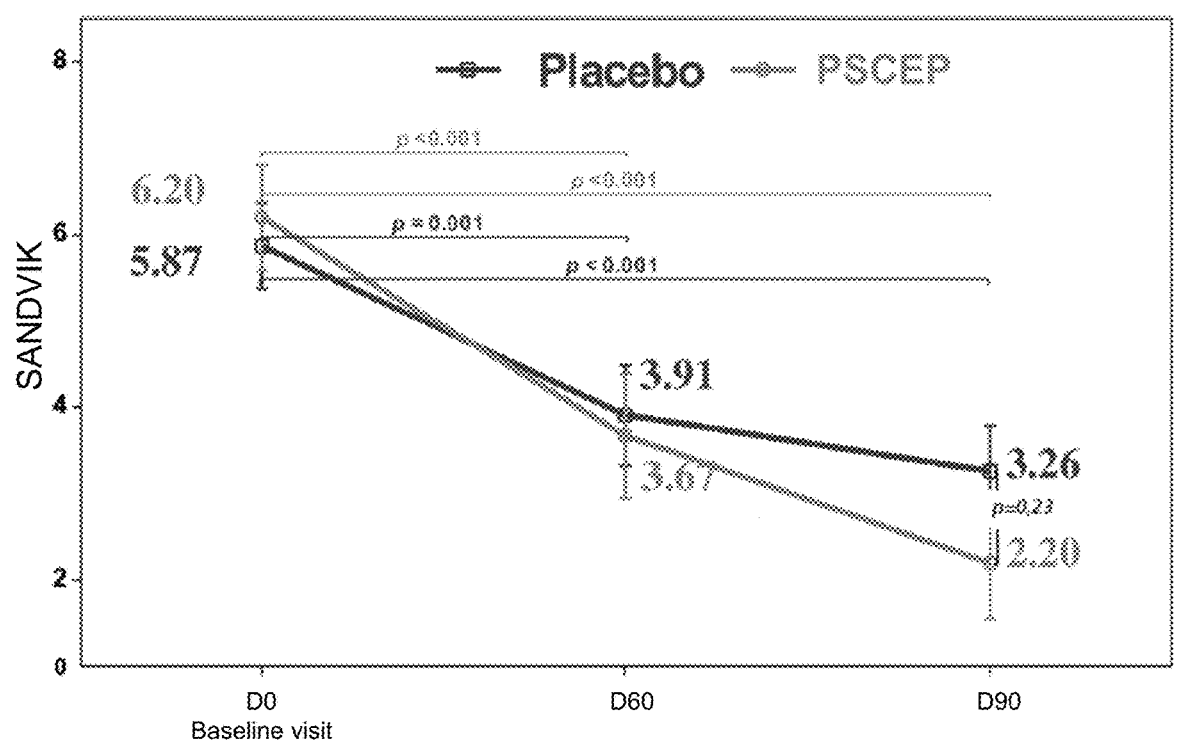
FIG. 13 shows the results obtained with the SANDVIK scale in the context of Example 6 on the efficacy of a composition according to the invention (according to Example 1=PSCEP; versus placebo) in women with urinary urgency (or urge) incontinence or mixed urinary incontinence before treatment (D0), after 60 days of treatment (D60) and after 90 days of treatment (D90).

As illustrated in FIG. 13, with the Sandvik index, there was a significant improvement after 90 days of treatment in the group with the composition according to the invention "PSCEP" compared to the baseline (p<0.001); however, there does not appear to be a statistically significant difference compared to the placebo group (p=0.23).

Example 7: Safety and Efficacy Study of a Composition According to the Invention in Women with Stress Urinary Incontinence (Randomised, Double-Blind, Placebo-Controlled Clinical Trial)

The aim of this study is to identify the response of a composition according to the invention in women diagnosed with stress incontinence.

In this study, 24 women were divided into two groups. One was treated with the composition according to the invention (according to Example 1=PSCEP in FIGS. 14-16) (n=12) and one was treated with placebo (n=12). Efficacy was assessed using validated questionnaires, namely the SANDVIK, MUH (Measurement of Urinary Handicap) and ICIQ-UI SF (International Consultation on Incontinence Questionnaire-Urinary Incontinence Short Form) scales.

No side effects were observed in any of the groups.

Results

Figure 14:
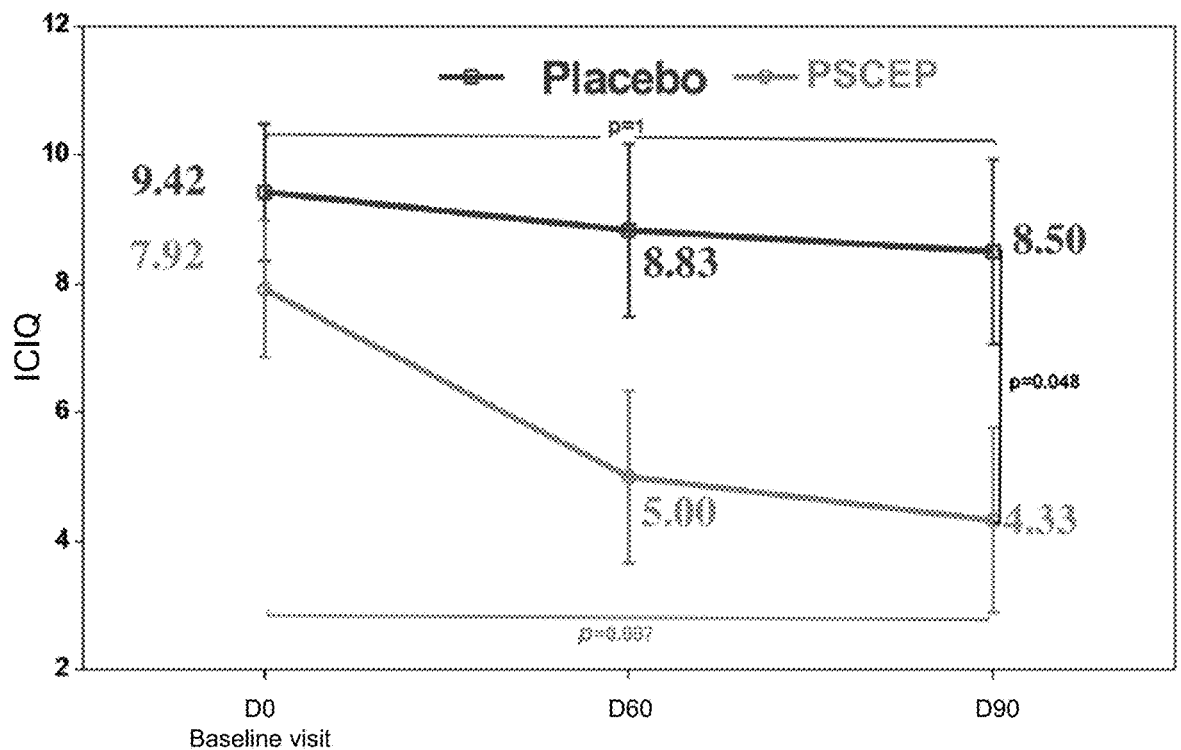
FIG. 14 shows the results obtained with the ICIQ scale in the context of Example 7 on the efficacy of a composition according to the invention (according to Example 1=PSCEP; versus placebo) in women with stress urinary incontinence before treatment (D0), after 60 days of treatment (D60) and after 90 days of treatment (D90).

As shown in FIG. 14, with the ICIQ-UI SF, a significant improvement in the group treated with the composition according to the invention "PSCEP" compared to the placebo group was observed after 3 months (p=0.048).

Figure 15:
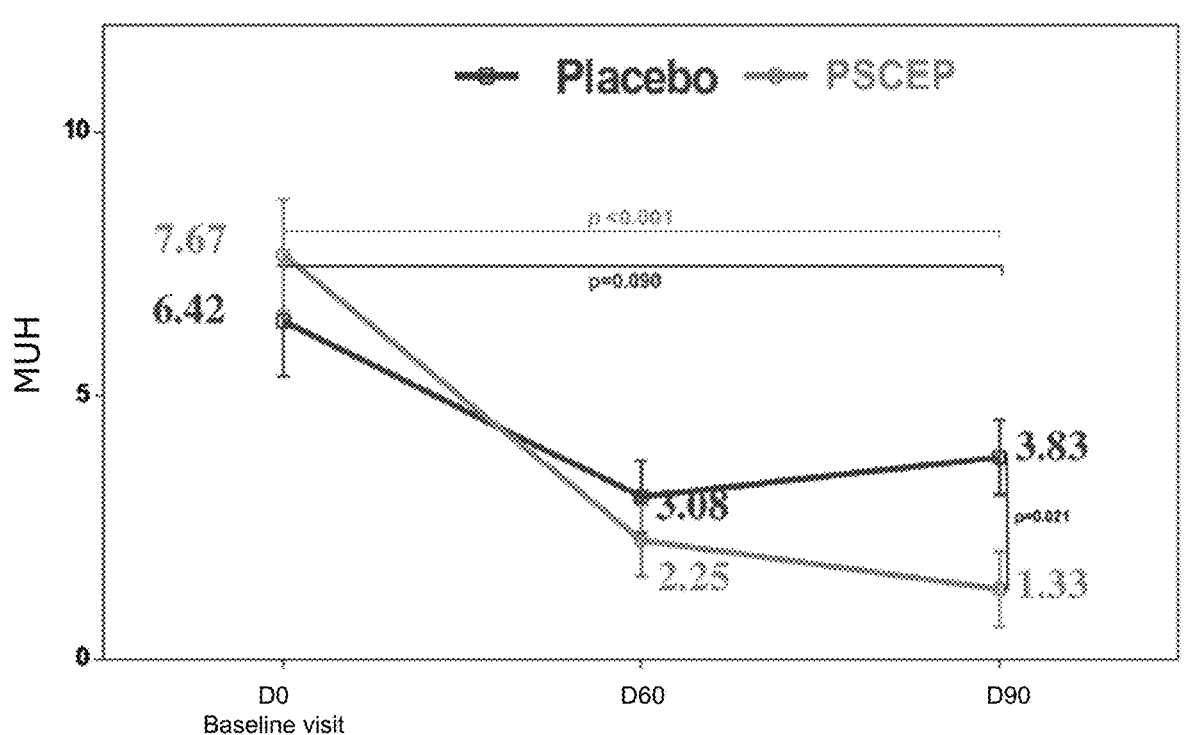
FIG. 15 shows the results obtained with the MUH scale in the context of Example 7 on the efficacy of a composition according to the invention (according to Example 1=PSCEP; versus placebo) in women with stress urinary incontinence before treatment (D0), after 60 days of treatment (D60) and after 90 days of treatment (D90).

As illustrated by FIG. 15, with MUH, a significant improvement in the group treated with the composition according to the invention "PSCEP" was observed (p<0.001) compared to the baseline, and a significant improvement after 3 months of treatment compared to the placebo group (p=0.021).

Figure 16:
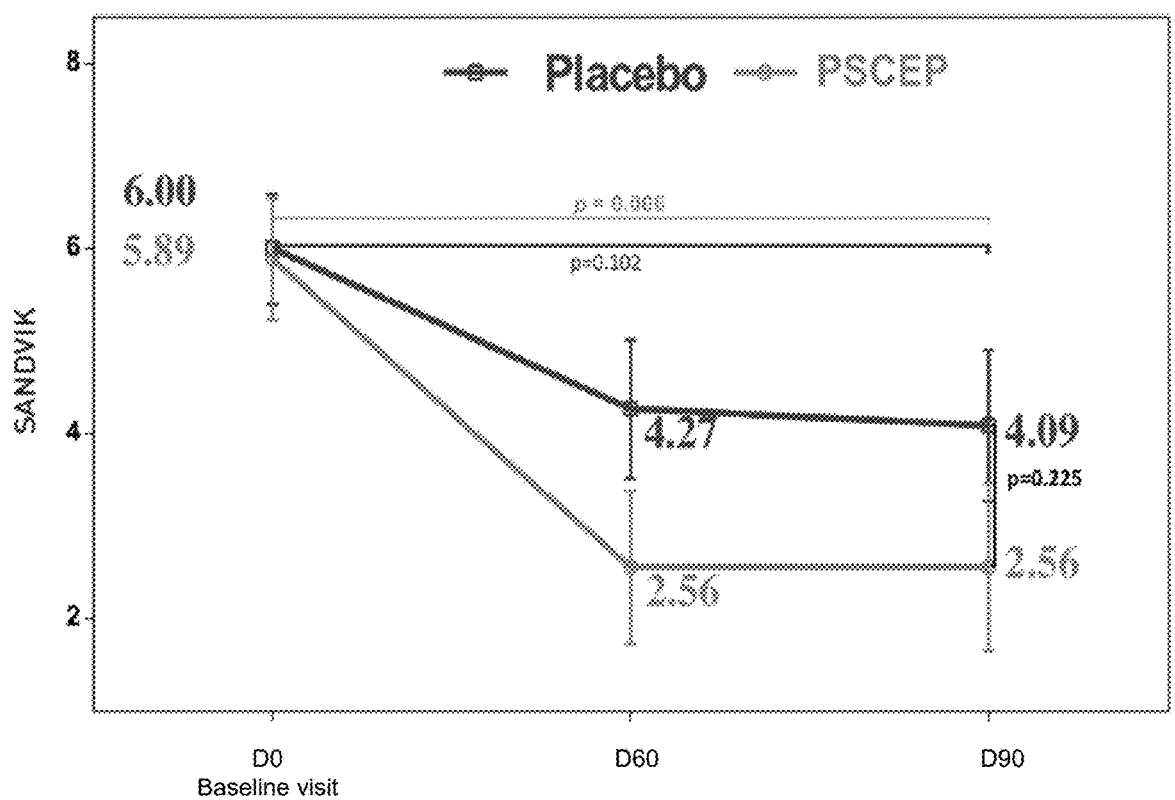
FIG. 16 shows the results obtained with the SANDVIK scale in the context of Example 7 on the efficacy of a composition according to the invention (according to Example 1=PSCEP; versus placebo) in women with stress urinary incontinence before treatment (D0), after 60 days of treatment (D60) and after 90 days of treatment (D90).

As illustrated in FIG. 16, with the Sandvik index, there was a significant improvement after 3 months of treatment in the group treated with the composition according to the invention "PSCEP" compared to inclusion (p=0.006). The placebo group showed no significant change at three months (p=0.102). However, there does not appear to be a statistically significant difference from the active group (p=0.225), probably due to the "insufficient" number of patients.

Example 8: Efficacy Study on the Nocturnal Micturition Frequency of a Composition According to the Invention In this study, 26 women with a diagnosis of symptoms of overactive bladder (OAB) presenting urinary incontinence due to urgency (or urge) or mixed urinary incontinence were treated with the composition according to the invention (according to Example 1) (n=26).

Figure 17:
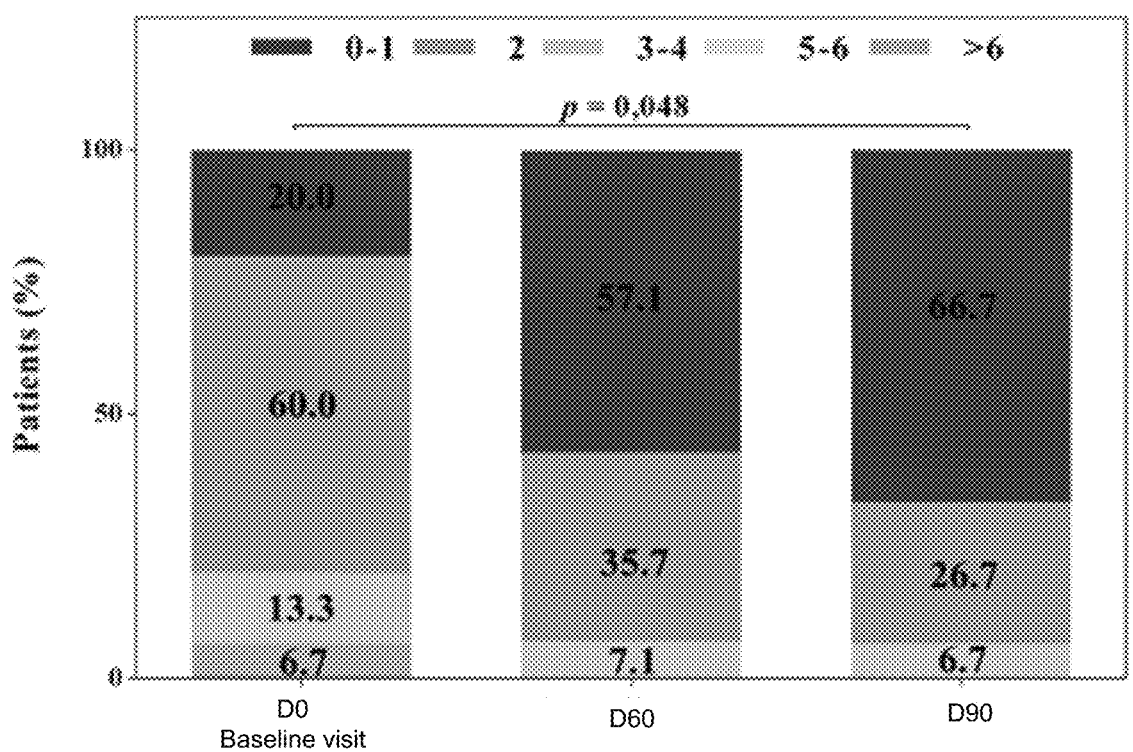
FIG. 17 shows the results obtained in the context of Example 8 on the efficacy of a composition according to the invention (according to Example 1) on the frequency of nocturnal micturition inducing an awakening in women with urinary urgency (or urge) incontinence or mixed urinary incontinence before treatment (D0), after 60 days of treatment (D60) and after 90 days of treatment (D90).

The "nocturnal micturition frequency" (or nocturia) corresponds to the totality of nocturnal micturition from the moment the patient goes to bed, taking into account the notion of awakening. The patients included in the study were classified into the following categories:
0 or 1 micturition per night (/night);
2 micturitions/night;
3-4 micturitions/night;
5-6 micturitions/night; or
more than 6 micturitions/night Results As illustrated in FIG. 17, the composition according to the invention (according to Example 1) significantly reduces the nocturnal micturition frequency of patients with urinary incontinence due to urgency (or urge) or mixed urinary incontinence:
with the composition according to the invention, the percentage of patients who had more than 6 micturitions per night at the start of the study (inclusion) disappears after 90 days of treatment: no patient is therefore still found in this category of more than 6 micturitions/night;
the percentage of those who had 3-4 micturitions per night is reduced by 50%;
the percentage of those who had 2 micturitions per night is reduced by 55%;
consequently, we then find 3.3 times more patients in the group of patients who presented 0-1 micturition per night.

Example 9: Study of the Activity of the Composition According to the Invention on the Muscarinic M3 Receptor Acetylcholine (Ach) is a neurotransmitter released by nerve cells to send signals to other cells, i.e. neurons, muscle cells and glandular cells. Acetylcholine exerts its effects by binding to receptors on the surface of these cells and activating them. There are two main classes of acetylcholine receptors, nicotinic and muscarinic, which are found in different tissues. In the bladder, the action of acetylcholine depends on the presence of muscarinic receptors which are located on the smooth muscle of the detrusor. Of the 5 types of muscarinic receptors called M1, M2, M3, M4 and M5, M2 and M3 are present in the bladder. M2 predominates in number and M3 is primarily the mediator of direct contractile responses to acetylcholine. In order for a healthy bladder to contract, acetylcholine is released from cholinergic nerves and activates the M3 receptor in the detrusor muscle, resulting in urine emptying when accompanied by relaxation of the release.

However, in hyperactive bladder (HAB), either more acetylcholine is released during normal bladder distension or acetylcholine receptors in the detrusor muscle are more sensitive. This leads to hyper contractility of the bladder. In the hyperactive bladder, pharmacological treatments are direct treatments, for example, administration of muscarinic receptor antagonists acting directly on M3 receptors.

The aim of the study is to test the activity of a composition according to the invention (according to Example 1) on the muscarinic M3 receptor using HEK293 cells which express the receptor endogenously (Crittenden C. et al., 2012, poster).

The composition according to the invention was tested alone, as well as each active ingredient of the composition (according to Example 1) taken independently.

The compounds were tested using a reference technology for profiling Gq GPCR compounds: called FLIPR Tetra, using the Screen Quest™ Fluo-8® No Wash Calcium Assay Kit (Euromedex).

Carbachol was used as a reference agonist and the intracellular increase in calcium was evaluated by FLIPR Tetra technology, as a readout for GPCR activation.

The robustness of the assay was confirmed by determining the affinity of carbachol in the various assays. Dose-response curves of carbachol (10 concentrations) were carried out during preliminary experiments and the calculated value of the EC50 of carbachol was used to test the antagonist activity of the composition according to the invention and of each active ingredient taken independently.

4-DAMP was used as a reference antagonist of the M3 receptor. The measured IC50 value is 0.26 nM or 0.00183 µg/ml as previously described (Dörje et al., 1991).

In each trial, positive (carbachol) and negative (4-DAMP or HBSS) controls were included to standardise the data, assess the robustness of the assay, and monitor efficacy.

HEK293 cells were seeded on a transparent Poly-D-Lysine flat base, 96 black 96-well plates incubated overnight at 37° C. with 5% $CO_2$. The next day, the plates were washed, the medium replaced with 50 µL physiological buffer (HBSS) and the cells loaded with Fluo-8 NW calcium dye (Molecular Devices). Fluo-8 NW dye was used according to the manufacturer's instructions: solubilised in DMSO, then mixed in assay buffer (1×), consisting of 10 mL of 10× Pluronic® F127 Plus (Molecular Devices) in 90 mL of HBSS buffer.

A dye solution (110 µL) was added to the cell plates and incubated at room temperature for 1.5 hours. Fluorescence was then measured using the FLIPR Tetra plate reader. During the first 10 seconds the baseline was read. After 10 seconds, 20 µL of different compounds were tested in 10 different doses and were added to the wells and the fluorescence was monitored for 3 minutes at Ex/Em=490/525 nm.

Then 10 seconds of a second baseline was measured, then 20 µL of carbachol (reference agonist) was added to the wells and the fluorescence was monitored for 3 minutes at Ex/Em=490/525 nm.

Results

Figure 18:
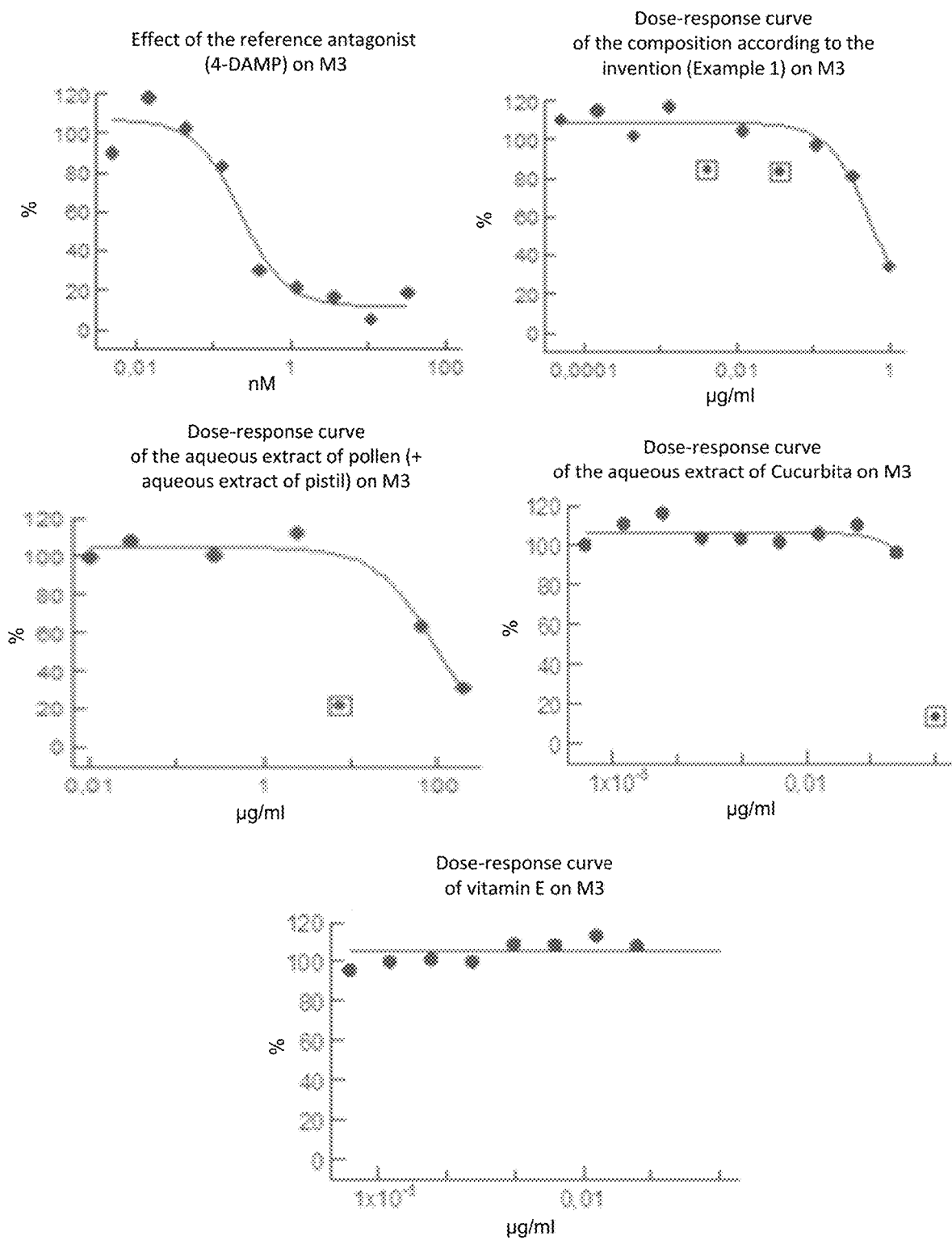
FIG. 18 shows the results obtained in the context of Example 9 on the activity of the composition according to the invention (according to Example 1), in a comparative manner with each active ingredient of the composition taken independently, on the muscarinic M3 receptor.

The dose-response curves of the composition according to the invention (according to Example 1), of each of the active ingredients tested independently and of the reference antagonist were normalised. The IC50 data are shown in the table below and shown in FIG. 18:

TABLE 6

| Compounds | IC50 µg/ml |
| --- | --- |
| 4-DAMP | 0.00183 |
| Composition according to the invention (according to Example 1) | 0.6 |
| Aqueous extract of pollen + aqueous extract of pistil (as in Example 1) | 96 |
| Aqueous extract of *Cucurbita* seeds (as in Example 1) | 1.19 |
| Vitamin E (as in Example 1) | >1 |

The results show that the IC50 value is significantly lower for the composition according to the invention than the IC50 value of each of the active ingredients tested independently.

Thus, according to these results, a significant antagonist activity on M3 is observed with the composition according to the invention, demonstrating a synergy between the different active ingredients of the composition according to the invention while each of the active ingredients taken independently has no (or very little) antagonist activity on M3; these M3 activity results also give a possible indication of the potential mechanism of action.

The invention claimed is:

1. A composition comprising:
   a pollen extract consisting of an aqueous pollen extract obtained from a plant mixture belonging to the family Pinaceae and Poaceae, wherein the aqueous pollen extract is obtained from a mixture of:
   45% to 90% aqueous extract of pollen of *Secale cereale* L. by weight of the total weight of the extract;
   1% to 35% aqueous extract of pollen of *Zea mays* L. by weight of the total weight of the extract;
   0.01% to 5% aqueous extract of pollen of *Pinus sylvestris* L. by weight of the total weight of the extract;
   3% to 30% aqueous extract of pollen of *Dactylis glomerata* L. by weight of the total weight of the extract,
   an aqueous extract of plant seeds belonging to the genus *Cucurbita* containing fatty acids at a content of less than 10% by weight of the total weight of the extract, vitamin E or its esters; and
   an aqueous extract of the pistil of *Zea mays* L.,
   wherein the composition treats lower urinary tract symptoms (LUTS) associated with the filling, micturition and/or post-micturition phases in women and, wherein the lower urinary tract symptoms (LUTS) associated with the filling, micturition and/or post-micturition phases in women is urinary incontinence.

2. The composition of claim 1, wherein the aqueous extract of *Cucurbita* seeds contains fatty acids at a content of between 5 and 8% by weight of the total weight of the extract.

3. The composition of claim 1, further comprising an active agent selected from the group consisting of manganese, and extracts of *Betula alba, Cerasus avium, Equisetum arvense, Phaseolus vulgaris, Achillea millefolium, Agropyron repens, Galium verum, Lavandula officinalis, Mentha piperita,* or *Urticaria dioica.*

4. The composition of claim 1, wherein the composition is in a form suitable for oral administration.

5. The composition of claim 4, wherein the form suitable for oral administration is selected from the group consisting of a tablet, a capsule, a soft capsule, a soft gel, a semi-solid, a solid, a liquid, and a powder.

6. A method for treatment of lower urinary tract symptoms (LUTS) associated with the filling, micturition and/or post-micturition phases in women, the method comprising:
providing an oral composition comprising:
a pollen extract consisting of an aqueous pollen extract obtained from a plant mixture belonging to the family Pinaceae and Poaceae, wherein the aqueous pollen extract is obtained from a mixture of:
45% to 90% aqueous extract of pollen of *Secale cereale* L. by weight of the total weight of the extract;
1% to 35% aqueous extract of pollen of *Zea mays* L. by weight of the total weight of the extract;
0.01% to 5% aqueous extract of pollen of *Pinus sylvestris* L. by weight of the total weight of the extract;
3% to 30% aqueous extract of pollen of *Dactylis glomerata* L. by weight of the total weight of the extract,
an aqueous extract of plant seeds belonging to the genus *Cucurbita* containing fatty acids at a content of less than 10% by weight of the total weight of the extract,
vitamin E or its esters; and
an aqueous extract of the pistil of *Zea mays* L.,
administering a daily dose to a woman in need thereof, and
wherein the lower urinary tract symptoms (LUTS) associated with the filling, micturition and/or post-micturition phases in women is urinary incontinence.

7. The method of claim 6, wherein the oral composition is in the form of a tablet, capsule, soft gel, semi-solid, solid, liquid, or powder.

8. The method of claim 6, wherein the daily dose is in a range of 360 mg to 1000 mg.

9. The method of claim 8, wherein the daily dose is administered for a period of at least one month.

10. The method of claim 6, wherein the urinary incontinence comprises stress urinary incontinence, urgent urinary incontinence, or combinations thereof.

11. The method of claim 10, wherein administering the daily dose is at a time of day for reducing the nocturnal micturition frequency inducing an awakening.

12. The method of claim 6, wherein
the aqueous pollen extract is 5% to 40 by weight of the total weight of the composition;
the aqueous extract of *Cucurbita* seed is 20% to 80% by weight of the total weight of the composition;
the vitamin E or its esters are 0.1% to 10% by weight of the total weight of the composition.

13. The method of claim 6, wherein aqueous extract of the pistil of *Zea mays* L. is present as 0.1% to 10% weight of the total weight of the extract.

14. The composition of claim 1, wherein
the aqueous pollen extract is 5% to 40 by weight of the total weight of the composition;
the aqueous extract of *Cucurbita* seed is 20% to 80% by weight of the total weight of the composition;
the vitamin E or its esters are 0.1% to 10% by weight of the total weight of the composition.

15. The composition of claim 1, wherein aqueous extract of the pistil of *Zea mays* L. is present as 0.1% to 10% weight of the total weight of the extract.

* * * * *